US012237056B2

(12) United States Patent
Bates et al.

(10) Patent No.: US 12,237,056 B2
(45) Date of Patent: Feb. 25, 2025

(54) EVENT DATA MODELLING

(71) Applicant: The Phoenix Partnership (Leeds) Ltd, Leeds (GB)

(72) Inventors: Chris Bates, Leeds (GB); Matthew Stickland, Leeds (GB); Frank Hester, Leeds (GB); Ankit Sharma, Leeds (GB)

(73) Assignee: The Phoenix Partnership (Leeds) Ltd, Horsforth (GB)

( * ) Notice: Subject to any disclaimer, the term of this patent is extended or adjusted under 35 U.S.C. 154(b) by 169 days.

(21) Appl. No.: 16/951,436

(22) Filed: Nov. 18, 2020

(65) Prior Publication Data

US 2021/0151140 A1    May 20, 2021

(30) Foreign Application Priority Data

Nov. 19, 2019   (GB) ..................................... 1916823

(51) Int. Cl.
    *G16H 10/60*      (2018.01)
    *G06N 20/00*      (2019.01)
    *G16H 40/60*      (2018.01)

(52) U.S. Cl.
    CPC ............. *G16H 10/60* (2018.01); *G06N 20/00* (2019.01); *G16H 40/60* (2018.01)

(58) Field of Classification Search
    CPC ............................... G16H 10/60; G16H 40/60
    See application file for complete search history.

(56) References Cited

U.S. PATENT DOCUMENTS

| 2006/0277074 | A1* | 12/2006 | Einav | G16H 20/30 705/3 |
| 2011/0313783 | A1* | 12/2011 | Sacco | G16H 50/80 705/2 |
| 2013/0197942 | A1* | 8/2013 | Chiu | G16H 40/67 705/3 |
| 2015/0006187 | A1* | 1/2015 | Draghi | G16H 40/63 705/2 |

(Continued)

OTHER PUBLICATIONS

Devlin, Hannah, Hospital develops AI to identify patients likely to skip appointments. The Guardian Apr. 12, 2019. Accessed at https://www.theguardian.com/society/2019/apr/12/hospital-develops-ai-to-identify-patients-likely-to-skip-appointments. 10 pages.

(Continued)

*Primary Examiner* — Rajesh Khattar
*Assistant Examiner* — Steven G. S. Sanghera
(74) *Attorney, Agent, or Firm* — Hamilton, Brook, Smith & Reynolds, P.C.

(57) ABSTRACT

A computer system for controlling access to medical resources, the system comprising at least one processor configured to: provide at least one trained machine learning model which has been trained on a training data set comprising healthcare event associated data, the at least one trained machine learning model having an input for receiving at least one operating data set associated with a particular healthcare event and an output for generating at least one value associated with the particular healthcare event; provide the at least one operating data set to the trained model and to receive the at least one value; and in dependence upon the at least one value, generate an indication of an assignment of medical resources for a patient associated with the event.

13 Claims, 14 Drawing Sheets

(56) References Cited

U.S. PATENT DOCUMENTS

| | | | |
|---|---|---|---|
| 2016/0144198 A1* | 5/2016 | Löf | G16H 40/20 600/1 |
| 2017/0177809 A1* | 6/2017 | Bull | G16H 50/30 |
| 2017/0352118 A1* | 12/2017 | Rodrigues De Moura Leitao | G16H 10/20 |
| 2018/0276340 A1* | 9/2018 | Dutkowski | A61K 9/2013 |
| 2018/0314798 A1* | 11/2018 | Hernandez | G16H 50/30 |
| 2018/0315182 A1* | 11/2018 | Rapaka | G06V 10/7747 |
| 2019/0189267 A1* | 6/2019 | Stoval, III | G06N 20/00 |
| 2019/0279767 A1 | 9/2019 | Bates | |
| 2019/0303758 A1* | 10/2019 | Meaker | G06N 3/0445 |
| 2020/0160986 A1* | 5/2020 | Vegas Santiago | G16H 10/60 |
| 2020/0229770 A1* | 7/2020 | Sedai | G16H 50/20 |
| 2020/0365268 A1* | 11/2020 | Michuda | G16H 50/30 |
| 2020/0411170 A1* | 12/2020 | Brown | G06N 20/00 |
| 2021/0082554 A1* | 3/2021 | Kalia | G06N 3/08 |
| 2021/0098090 A1* | 4/2021 | Thomas | G16H 50/30 |

OTHER PUBLICATIONS

Extended European Search Report in European Patent Application No. 20196572.0 dated Mar. 16, 2021, 12 pages.

\* cited by examiner

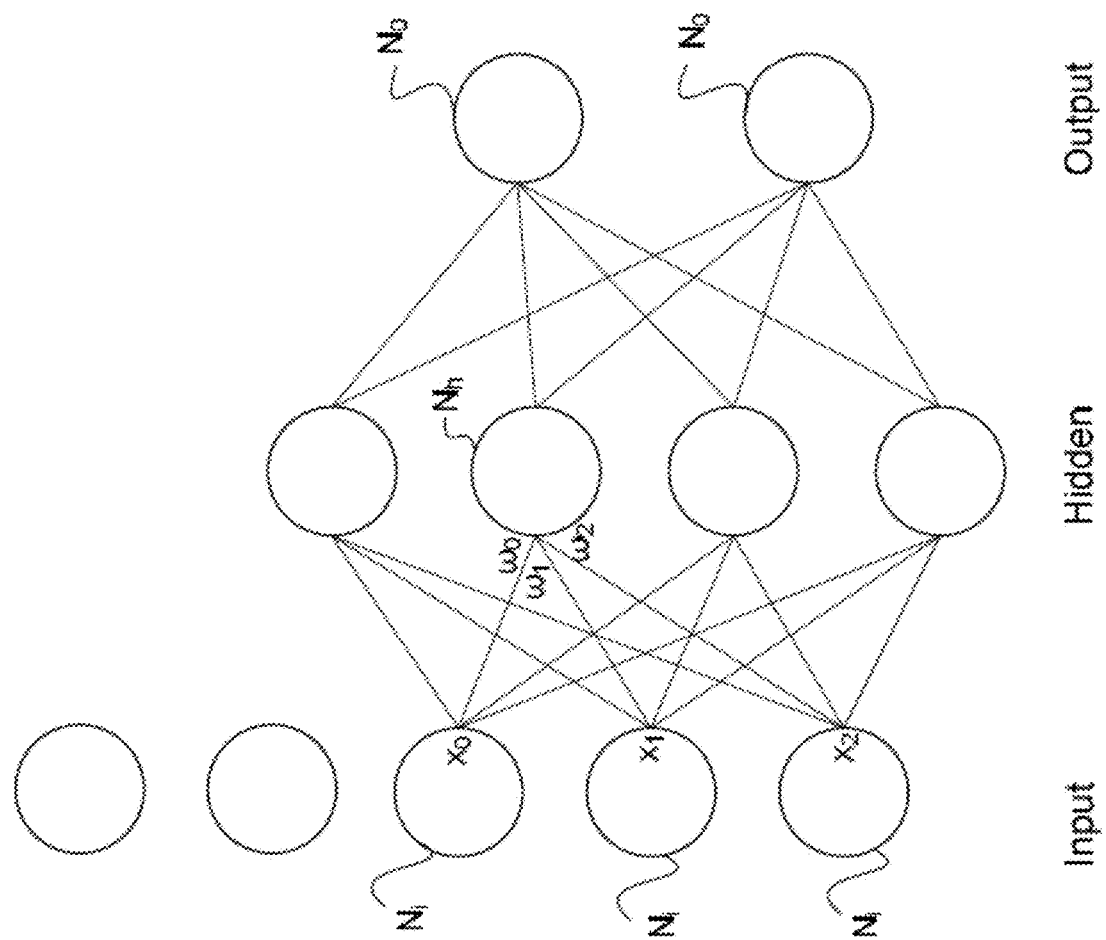

EVENT DATA MODELLING

CROSS-REFERENCE TO RELATED APPLICATION(S)

This application claims priority to GB 1916823.6, which was filed on Nov. 19, 2019, and is incorporated herein by reference in its entirety for all purposes.

TECHNICAL FIELD

The present disclosure relates to systems for accessing medical resources and treatment.

BACKGROUND

Hospitals and medical centres are equipped with extensive resources for treating patients, including general practitioners and specialists with access to specialist equipment. Existing patient access models rely on individuals presenting themselves to a hospital or medical centre. At a medical centre, they may have an appointment to attend. At a hospital, they may present at an emergency unit. At the first point of call, patients describe their symptoms, and in an emergency context there may be a triaging system in place.

It is often the case that medical resources may not be appropriately allocated for patients. The medical resources that are assigned for a patient for their treatment may depend upon accurate diagnosis of a patient condition, which may be lacking in an initial triage stage. Furthermore, appropriate control over the access to medical resources may depend upon predictions of the use of medical resources by that patient, e.g. their length of stay in hospital.

Where there is a triaging system in place, the detailed process may take many hours to accomplish. In the meantime, relevant medical resources, such as scanning equipment, specialists, x-ray machines, may be standing idle.

What is needed is a way to control access to medical resources and treatments to optimise their use.

SUMMARY

The use of trained models on curated health related event data can significantly improve access to medical resources and treatment.

According to a first aspect, there is provided a computer system for controlling access to medical resources, the system comprising at least one processor configured to: provide at least one trained machine learning model which has been trained on a training data set comprising healthcare event associated data, the at least one trained machine learning model having an input for receiving at least one operating data set associated with a particular healthcare event and an output for generating at least one value associated with the particular healthcare event; provide the at least one operating data set to the trained model and to receive the at least one value; and in dependence upon the at least one value, generate an indication of an assignment of medical resources for a patient associated with the event.

In some embodiments, the at least one processor is configured to generate the at least one operating data set in dependence upon data input at a client device.

In some embodiments, the at least one processor is configured to: request data from a data store in dependence upon data input at a client device; and generate the at least one operating data set in dependence upon the data requested from the data store.

In some embodiments, the data requested from the data store comprises data retrieved from an electronic health record of the patient.

In some embodiments, the data requested from the data store comprises an indication of the availability of healthcare resources.

In some embodiments, the at least one value comprises at least one probability associated with one or more diagnoses for the patient.

In some embodiments, the at least one value comprises an indication of available healthcare resources.

In some embodiments, the at least one value comprises a predicted outcome associated with the particular healthcare event.

In some embodiments, the indication of the assignment of medical resources comprises a medical appointment booking.

In some embodiments, the indication of the assignment of medical resources comprises at least one of: an indication of a selected test for a patient; and an indication of a selected treatment for a patient.

In some embodiments, the at least one trained machine learning model comprises a plurality of machine learning models, each of the plurality of models having an input for receiving an operating data set associated with the particular healthcare event and an output for generating at least one value associated with the particular healthcare event, wherein the at least one processor is configured to: provide a first operating data set to a first of the models to generate a first at least one value; provide a second operating data set to a second of the models to generate a second at least one value; and in dependence upon both the first at least one value and the second at least one value, generate an indication of an assignment of medical resources for the patient associated with the event.

In some embodiments, the at least one processor is configured to: in dependence upon the first at least one value, generate an initial indication of an assignment of medical resources for the patient; subsequently, perform the providing the second operating data set to the second of the models to generate the second at least one value; and subsequently, in dependence upon the second at least one value, generate the indication of the assignment of medical resources for the patient.

In some embodiments, the initial indication of the assignment of medical resources for the patient comprises an indication of a test for the patient, wherein the at least one processor is configured to: subsequently, receive data comprising results from the test for the patient; and generate the second operating data set in dependence upon the results from the test for the patient.

In some embodiments, the computer system comprises a client device and a back-end system.

In some embodiments, the back-end system comprises at least one processor configured to: perform the providing the at least one operating data set to the at least one trained model and receiving the at least one value; cause the at least one value to be provided to the client device, wherein the client device comprises at least one processor configured to, perform the generation of the indication of the assignment of medical resources in dependence upon the at least one value.

In some embodiments, the back-end system comprises at least one processor configured to: perform the providing the at least one operating data set to the at least one trained model and receiving the at least one value; perform the generation of the indication of the assignment of medical resources in dependence upon the at least one value; and provide the indication of the assignment of medical resources to the client device.

In some embodiments, the at least one processor is configured to provide one or more further operating data sets to the at least one trained model to obtain one or more further values, wherein each of the one or more further operating data sets is associated with a different patient, wherein the generation of an indication of an assignment of medical resources for the patient associated with the event is performed in dependence upon the one or more further values.

In some embodiments, the at least one value comprises an indication of a value of assigning a first medical resource to the patient associated with the event, wherein at least one of the one or more further values comprises an indication of a value of assigning the first medical resource to a further patient, wherein the generation of an indication of an assignment of medical resources for the patient associated with the event comprises comparing the value of assigning the first medical resource to the patient associated with the event with the value of assigning the first medical resource to the further patient so as to prioritise access to the first medical resource.

In some embodiments, the at least one processor is configured to provide a third operating data set to the at least one trained model to obtain an indication of a value of assigning a second medical resource to the patient associated with the event, wherein the generation of the indication of the assignment of medical resources for the patient associated with the event is performed in dependence upon the value of assigning the second medical resource to the patient associated with the event.

According to a second aspect, there is provided a computer implemented method for controlling access to medical resources, the method comprising: provide at least one trained machine learning model which has been trained on a training data set comprising healthcare event associated data, the at least one trained machine learning model having an input for receiving at least one operating data set associated with a particular healthcare event and an output for generating at least one value associated with the particular healthcare event; provide the at least one operating data set to the trained model to receive the at least one value; and in dependence upon the at least one value, generate an indication of an assignment of medical resources for a patient associated with the event.

In some embodiments, the method comprises generating the at least one operating data set in dependence upon data input at a client device.

In some embodiments, the method comprises: requesting data from a data store in dependence upon data input at a client device; and generating the at least one operating data set in dependence upon the data requested from the data store.

In some embodiments, the data requested from the data store comprises data retrieved from an electronic health record of the patient.

In some embodiments, the data requested from the data store comprises an indication of the availability of healthcare resources.

In some embodiments, the at least one value comprises at least one probability associated with one or more diagnoses for the patient.

In some embodiments, the at least one value comprises an indication of available healthcare resources.

In some embodiments, the at least one value comprises a predicted outcome associated with the particular healthcare event.

In some embodiments, the indication of the assignment of medical resources comprises a medical appointment booking.

In some embodiments, the indication of the assignment of medical resources comprises at least one of: an indication of a selected test for a patient; and an indication of a selected treatment for a patient.

In some embodiments, the at least one trained machine learning model comprises a plurality of machine learning models, each of the plurality of models having an input for receiving an operating data set associated with the particular healthcare event and an output for generating at least one value associated with the particular healthcare event, wherein the at least one processor is configured to: provide a first operating data set to a first of the models to generate a first at least one value; provide a second operating data set to a second of the models to generate a second at least one value; and in dependence upon both the first at least one value and the second at least one value, generate an indication of an assignment of medical resources for the patient associated with the event.

In some embodiments, the at least one processor is configured to: in dependence upon the first at least one value, generate an initial indication of an assignment of medical resources for the patient; subsequently, perform the providing the second operating data set to the second of the models to generate the second at least one value; and subsequently, in dependence upon the second at least one value, generate the indication of the assignment of medical resources for the patient.

In some embodiments, the initial indication of the assignment of medical resources for the patient comprises an indication of a test for the patient, wherein the at least one processor is configured to: subsequently, receive data comprising results from the test for the patient; and generate the second operating data set in dependence upon the results from the test for the patient.

In some embodiments, the method is implemented in a computer system comprises a client device and a back-end system.

In some embodiments, the method comprises: the back-end system providing the at least one operating data set to the at least one trained model and receiving the at least one value; the back-end system causing the at least one value to be provided to the client device; the client device performing the generation of the indication of the assignment of medical resources in dependence upon the at least one value.

In some embodiments, the method comprises: the back-end system providing the at least one operating data set to the at least one trained model and receiving the at least one value; the back-end system performing the generation of the indication of the assignment of medical resources in dependence upon the at least one value; and the back-end system providing the indication of the assignment of medical resources to the client device.

In some embodiments, the method comprises providing one or more further operating data sets to the at least one trained model to obtain one or more further values, wherein each of the one or more further operating data sets is associated with a different patient, wherein the generation of an indication of an assignment of medical resources for the patient associated with the event is performed in dependence upon the one or more further values.

In some embodiments, the at least one value comprises an indication of a value of assigning a first medical resource to the patient associated with the event, wherein at least one of the one or more further values comprises an indication of a value of assigning the first medical resource to a further patient, wherein the generation of an indication of an assignment of medical resources for the patient associated with the event comprises comparing the value of assigning the first medical resource to the patient associated with the event with the value of assigning the first medical resource to the further patient so as to prioritise access to the first medical resource.

In some embodiments, the method comprises providing a third operating data set to the at least one trained model to obtain an indication of a value of assigning a second medical resource to the patient associated with the event, wherein the generation of the indication of the assignment of medical resources for the patient associated with the event is performed in dependence upon the value of assigning the second medical resource to the patient associated with the event.

BRIEF DESCRIPTION OF DRAWINGS

FIG. 4 is a simplified schematic view of a neural network;

DETAILED DESCRIPTION

In the following, access to medical treatment and resources may be better controlled by using trained machine learning models and new and curated data associated with an event. Techniques for generating training data to train the models are also presented. An event in this context may be understood to mean an "episode of care" in which a patient interacts with a provider of healthcare. An event, therefore, includes an appointment, hospital admissions, surgery, out of hour's phone calls, presentation of a patient in an emergency department, etc. Information regarding past occurrences of these events, along with associated data, is used to generate training data sets to train machine learning models.

The trained machine learning models are used to determine parameters governing access to particular medical resources.

As an example, a trained model may suggest a diagnosis for a patient. The diagnostic output of the model is then used by the computer system to determine parameters governing access to medical resources required to treat the condition that has been suggested for the patient. Information related to a particular event is collected and processed to produce a training data set, which is then used to train a model which will be able to generate predictions of use of certain medical resources in various contexts.

As another example, a trained model may provide a prediction of the likelihood of a patient's discharge from hospital being delayed. This likelihood output by the model is then used by the computer system to determine a parameter governing access to medical resources. For example, if a prediction is made by the model that a delayed discharge is likely, the computer system may allocate or suggest additional medical resources for the patient.

Figure 1:
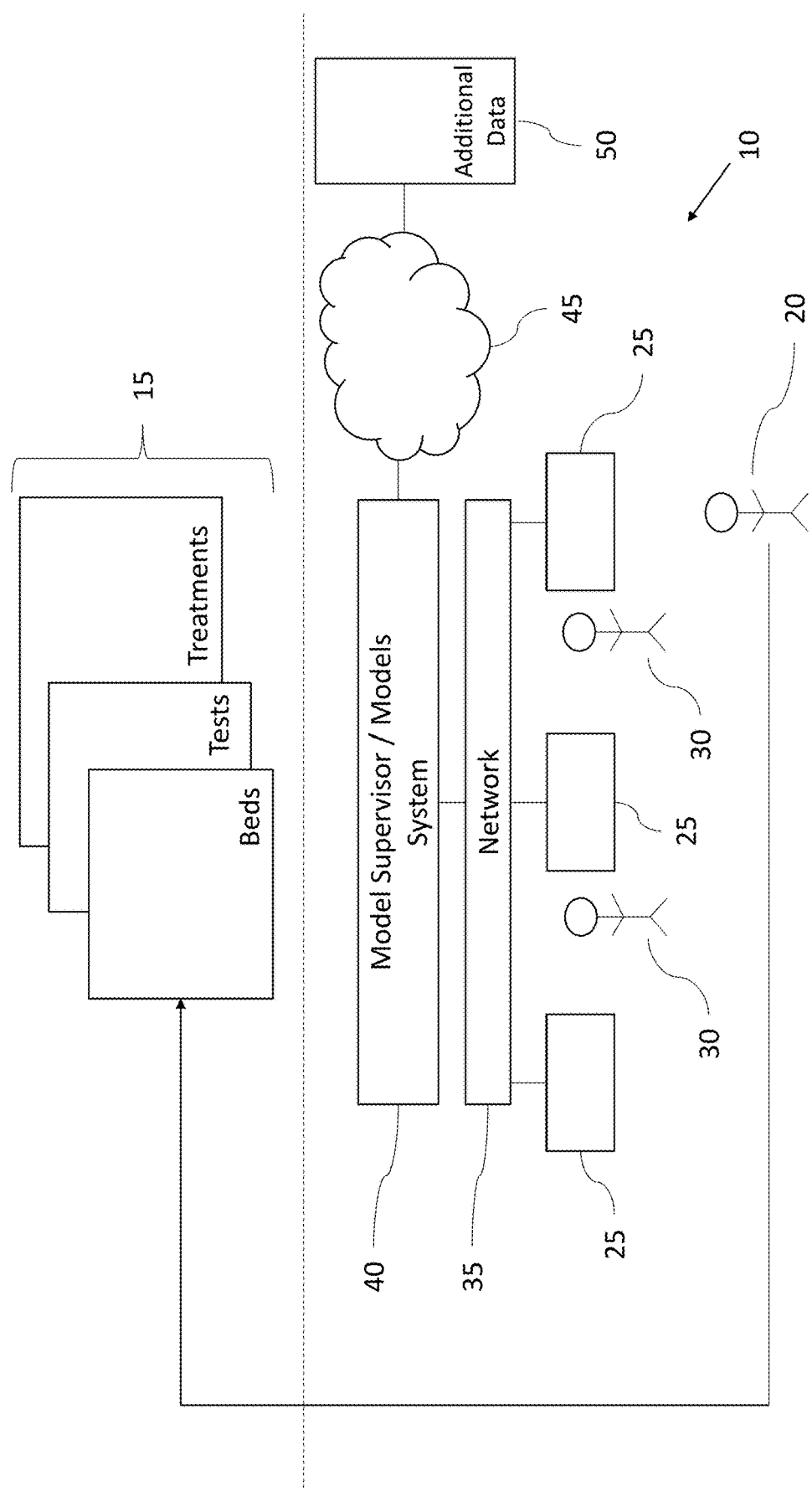
FIG. 1 is a schematic illustration of the operation of a system for controlling access to medical resources using machine learning models.

Reference is made to FIG. 1, which illustrates an example of the use of a system 10 of event related information during an operating phase to provide inputs to machine learning models so as to produce outputs that are used to control access to medical resources 15. The medical resources 15 may include beds, tests, and treatments that are available for a patient 20.

The system 10 in this case, comprises one or more triaging terminals 25 that are configured to receive data input to the terminal. This 'input data' may be associated with a medical emergency in the case that the patient presents at the accident and emergency department of a hospital. The information that is input to the triaging terminal 25 may, for example, comprise one or more of: a patient identifier, information regarding a patient's condition, time of day at which the patient presented, certain biographical details of a patient (e.g. age or gender), location of the event, whether the event has been flagged as urgent, the symptoms the patient is currently experiencing, any recent history of travel, any medication taken within a certain time period (e.g. the last 48 hours). This information may be input to an appropriate triaging terminal 25 by one or more healthcare staff 30. Each of the triaging terminals 25 comprises a computer system, which may be a general purpose personal computer or a special purpose computing device. An example of a computing device 700, which may provide each triaging terminal 25 is shown, and later described, with respect to FIG. 9. The computing device 700 more broadly may be any client device, such as a phone or tablet. An example of a system 600, which may provide the system 40, is shown and later described with respect to FIG. 8. The system 40 is a back-end system for processing machine learning models in response to information received from a client device 25.

The system 10 comprises a network 35, which receives packets from the triaging terminals 25 and provides the packets to a machine learning system 40. The network 35 includes an internal network, which is linked to the triaging terminals 25. In the case that the machine learning system 40 is provided at a remote location from the triaging terminals 25, the network 35 further includes an external network enabling communication with the machine learning system 40 at the remote location.

The machine learning system 40 provides a model supervisor and one or more machine learning models. The model supervisor receives the input information from the appropriate triaging terminal 25 and selects an appropriate machine learning model to perform processing so as to control access to medical resources 15.

The model supervisor executed by the machine learning system 40 may determine that, in order to run a particular machine learning model to assign medical resources, further information is required. The information may, for example, be data from a patient's electronic health record, data relating to the current use of resources in the hospital (e.g. number of beds currently occupied), environmental data, etc. This additional data is stored in one or more data stores 50. The additional data stored in one or more data stores 50 is pre-existing data that exists before the input data is input to one of the triaging terminals 25. This additional data may comprise patient's date of birth, gender, blood type, address, long-term conditions they are living with, repeat medication they are taking. In response to determining that the additional data is required, the machine learning system 40 sends a request over the network 45 to the one or more data stores 50. The requested data is returned to the machine learning system 40.

In some cases, data retrieved at the machine learning system 40 may be used to derive additional information. For example, if a patient postcode is provided to the system 10 from one of additional data sources 50, the patient post code is used to perform a look up into another of said additional data sources 50 to obtain a social deprivation score for an area.

In some cases, the machine learning system 40 determines that it needs more input data in order to proceed and obtain a result from one or more machine learning models, the machine learning system 40 may issue a request for further information from the relevant triaging terminal 25. This could be, for example, a request to collect information regarding additional symptoms from the patient or to gather the patient's ethnicity. This data is entered at the terminal 25 and returned to the model system 40.

In some cases, the input values required for input to the selected one or more models may not be available in either the data items received from the terminal 25 nor in the data items received from the additional data sources 50. In this case, the input values may be imputed from the available data items, even if those data items do not expressly map to the input values. For example, in the situation where a patient's body mass index is not known, it may be imputed using a formula based on the patient's gender, age, and social deprivation score. By imputing the input values for a model indirectly from the data items, the selected one or more models may be run when the data items directly encoding for a particular feature are unavailable. In other cases, if the data is unavailable, then the system 40 may determine not to run the model. This may occur if the system 40 is unable to impute the values from available data items indirectly. In this case, the system 40 returns an error code to the terminal 25, which is displayed on a screen of the terminal.

Together, the requested additional information retrieved from data store 50 along with the initial event details input to the terminal 25 form a set of data items associated with the event. Each of these data items comprises a descriptor indicating a particular feature, e.g. a patient symptom, a number of beds available in the hospital, the number of staff available, the competencies/skills of the available staff, or the type of diagnostic test available in the hospital (e.g. X-ray, ultrasound, MRI, CT scans). The set of data items are processed to produce a set of input values for a machine learning model. In some embodiments, the data received in the initial event details and additional information is processed by the machine learning system 40 to form a set of data items in a standard format before being passed to a conversion module in the machine learning system 40 to produce input values for a selected model. The set of data items provided to the conversion module is described in more detail later in this description.

The process of producing the input values for a model is explained in more detail below. The input values (or 'scores') together form an operating data set for the event that can be provided to a model during an operating phase to obtain an output. A conversion module in system 40 provides the determined scores to the model supervisor in system 40. These scores are used as inputs to a selected one or more machine learning models to obtain one or more outputs. Therefore, together, the data input at the terminal 25 and the data retrieved from data store 50 are used to derive a plurality of input values for input to a machine learning model to obtain an output used to assign medical resources 15 for the patient 20.

When the selected machine learning model has been applied to determine an output, the output is used to control the assignment of medical resources. Terminal 25 outputs an indication of an assignment of medical resources 15 for use by the patient 20. For example, the terminal 25 may output an indication of a particular treatment or test to be carried out for the patient. The terminal 25 may output an indication that a patient is to be admitted to hospital.

In order to produce the indication of the assignment of medical resources for use by the patient 20, the machine learning system 40 or the terminal 25 may perform processing of the output from one or more of the machine learning models. For example, a set of output values from a model may represent the probability of a patient having particular condition. These probabilities are post-processed to produce an assignment of medical resources for the patient. In one example, the output values may indicate that the patient has a certain threshold probability of heart problems. In response to this indication, the terminal 25 outputs an instruction that a CT scan is to be carried out for the patient 20. The post processing of the output/s from the machine learning model/s can be performed by the machine learning system 40, with the indication of the assignment of medical resources being provided to the terminal 25. Alternatively, system 40 may send the output/s from the machine learning model/s to the terminal 25, which itself determines the indication of the assignment of medical resources.

Although the system 10 illustrated in FIG. 1 may be applied to determine how to triage patients who present in an accident and emergency department, it is not so limited, but may be applied to assign medical resources for patients in different contexts, such as the assignment of resources for patients already admitted to hospital. These different contexts are described in further detail below.

Figure 1A:
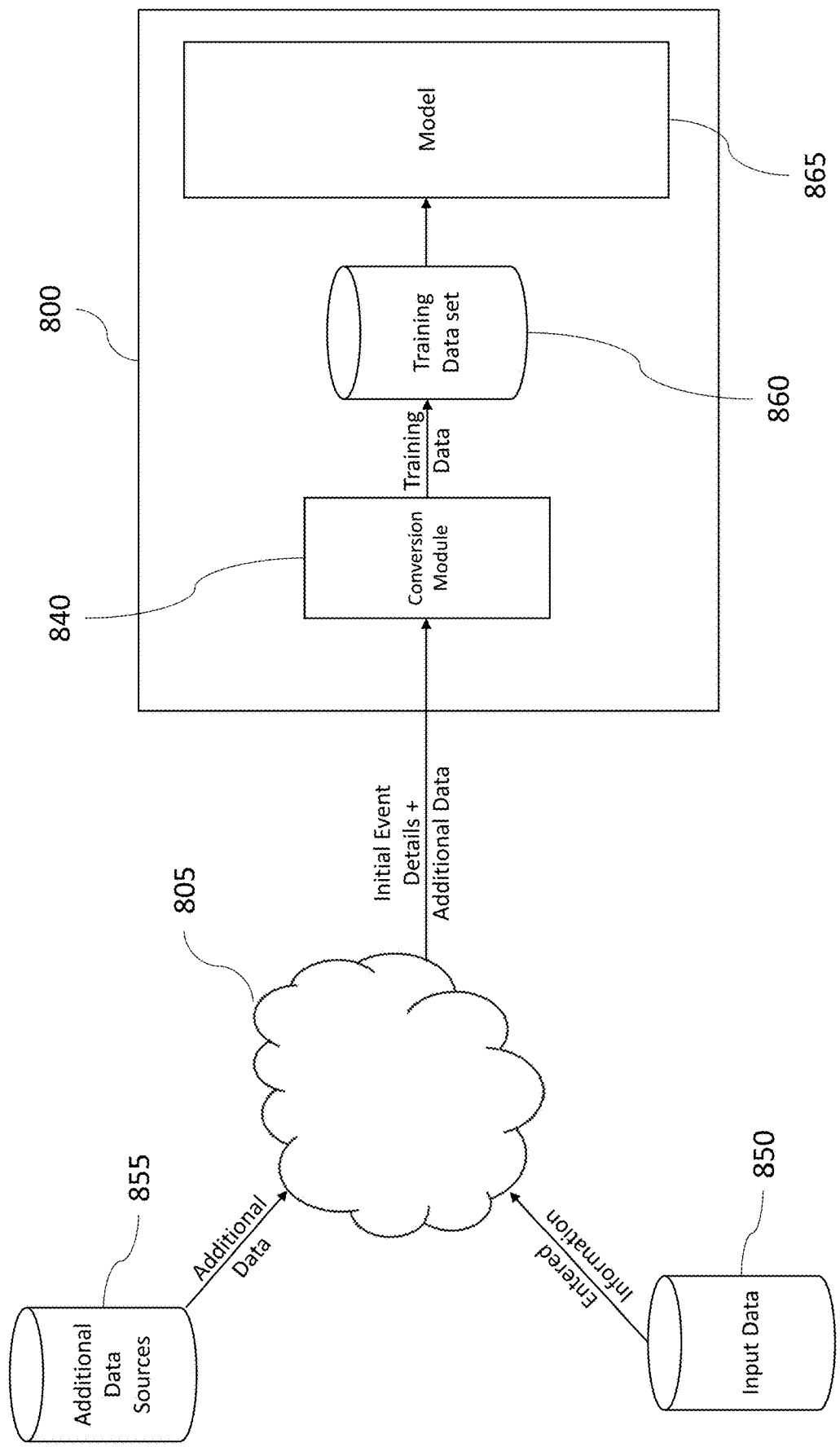
FIG. 1A is a schematic illustration of the collection of data for training a machine learning model.

Reference is made to FIG. 1A, which illustrates the use of a system 800 during a training phase to train one of the machine learning models that are operated by the machine learning system 40 during an operating phase as discussed above with respect to FIG. 1. An example of a system 600, which may provide the system 800, is shown and later described with respect to FIG. 8.

Input data is retrieved from a store 850. The input data store 850 is a database storing information associated with the event. This may be information entered when a patient presents at a triaging terminal 25 as shown in FIG. 1A. The information in the input data store 850, can comprise information entered by a patient when an event is booked. It can be information entered by a patient prior to an appointment, for example, by the patient entering the information on their phone prior a consultation. The information can, additionally or alternatively, comprise information provided upon presentation of the patient at a healthcare service provider. The information in input data store 850 may comprise data collected and stored a long time prior to the event but, which is immediately available at the client device. This includes biographical information regarding the patient, such as the patient's sex or address.

The input data held in store 850 comprises at least initial event details providing records of episodes of care. The initial event details comprises the basic information regarding an episode of care, such as a hospital admission, an urgent care attendance, an outpatient appointment, a GP appointment, or a home visit. The initial event details may be provided when an event (e.g. an appointment) is booked or when a patient presents in an emergency department. The initial event details comprise information, such as the date, time, location, patient ID, identifying the event as such. The input data held in store 850 may also comprise information about the patient—such as symptoms, age, gender, long-term conditions, current repeat medication—that is entered along with the information detailing the event.

Additional data/external data is also retrieved from additional data sources 855. The additional data is associated with specific events identified in the initial event details. For example, the additional data may comprise an indication of pollution or pollen levels over recent days in the area of the event. It may comprise data about current infectious disease statistics in the area at which one of the events took place.

The additional data may comprise health record data of a patient that isn't entered as part of the input data that is held in store 850. This additional data may comprise patient's date of birth, gender, blood type, address, long-term conditions they are living with, and the repeat medication they are taking.

The system 800 is configured to request some or all of the additional data in dependence upon the required input values for the model being trained. For example, if the model 865 requires the social deprivation index at the location of the event, the system 800 issues a request for this information and the information is returned to the system 800 from the additional data sources. The additional data is also retrieved in dependence upon the initial event details. The system 800 receives the initial event details and uses information in the initial event details to formulate a request for additional data from additional data sources. For example, the system 800 uses the indication of the location of the event in the initial event details to retrieve the social deprivation index at that location from the additional data sources 855. The initial event details and additional data are, therefore, provided to the system 800. Together they form a raw data set comprising data associated with different events.

The initial event details for each event comprise a patient identifier associated with the event. These identifiers may be included in requests (e.g. requests for a patient's health record) for additional data sent to data sources 855, and therefore used to select the appropriate additional data from the additional data sources 855.

Together, the requested additional information along with the initial event details form a set of data items associated with the event. Each of these data items comprises a descriptor indicating a particular feature, e.g. a patient symptom, or a number of beds available in the hospital. In some embodiments, the data received in the initial event details and additional information is processed by the system 800 to form a set of data items in a standard format before being passed to the conversion module 840a to produce the training data.

The set of data items used for generating both the training and operating data for any particular event may comprise a very large number of data items, contain descriptors spanning many categories, e.g. weather, pollen count, patient demographic information, patient health information, social deprivation, operational hospital statistics, pollution data. Sets of data items are established for a number of different events. The number of events for which the training data set is established may comprise many thousands, up to hundreds of millions of events.

Each of the data items in one of the sets of data items may indicate one or more of the following: deprivation score of the area in which the patient lives or in which the event is scheduled to take place; the age of the patient; the ethnicity of the patient; rurality of the area in which the patient lives or in which the event is scheduled to take place; the sex of the patient; time and date associated with the event; number of healthcare events associated with the patient that have occurred with a predefined time period (e.g. number of hospital admissions within the last two years); amount of time that the patient has been registered at the practice at which the event is scheduled to take place; whether the event has been flagged as urgent; whether the patient has children; mental health diagnoses for the patient; frailty score; number of people registered at the healthcare service/facility where the event takes place; distance between the patient's home and the event takes place; whether the patient's first language is English or not; length of time that the healthcare staff will have already spent working before attending to the patient on that day; the number of healthcare staff available on a particular day; and the number of healthcare staff of a relevant speciality that are available on a particular day.

In some embodiments, each of the data items falls into at least one of the following categories: patient-level clinical data; patient-level administrative data; patient-level demographic data; organisational-level data; and additional temporal data.

Patient-level clinical data includes indications of diagnoses, symptoms, medication, immunisations, laboratory tests, and numeric clinical results. It includes both historical information (e.g. long-term conditions that the patient is living with) and acute clinical information at a point in time (e.g. the presenting complaint of a patient in an emergency department).

Patient-level administrative data is drawn from databases of electronic medical records and healthcare information systems. It includes, for example, information regarding appointments (such as outpatient appointments and GP appointments), hospital admissions, discharges, delays, urgent care attendances, and referrals for specialist care. Each of these data items has several different components, including a time associated the event. For example, a hospital admission for a patient includes details of the date and time of admission, the length of stay, the admission source, and whether it was planned or unplanned.

Patient-level demographic data is drawn from databases of electronic medical records and healthcare information systems. It includes indicators of one or more of: a patient's gender, marital status, occupation, deprivation index, rural/urban classification, spoken-language, and ethnicity.

Organisational-level data contains information about the healthcare institution associated with the event, such as its facilities, and its staff. For example, for a hospital this data may include the number of beds, the number and type of wards, the medical specialties that the hospital provides care for, the number of consultants, the number of nurses, the available treatment facilities, and the diagnostic testing facilities the hospital provides.

Additional temporal data contains time-dependent data regarding the event. This data describes the state of healthcare facilities and/or external systems at a given point in time. For example, it includes information about the number of free beds in a hospital at a given time, the number of nursing staff on duty, or the number of patients waiting to be seen in the emergency department. For external systems, the data may include the time of day, the time of year, weather data, pollution data, regional immunisation rates, and/or geographic population levels.

Figure 1B:
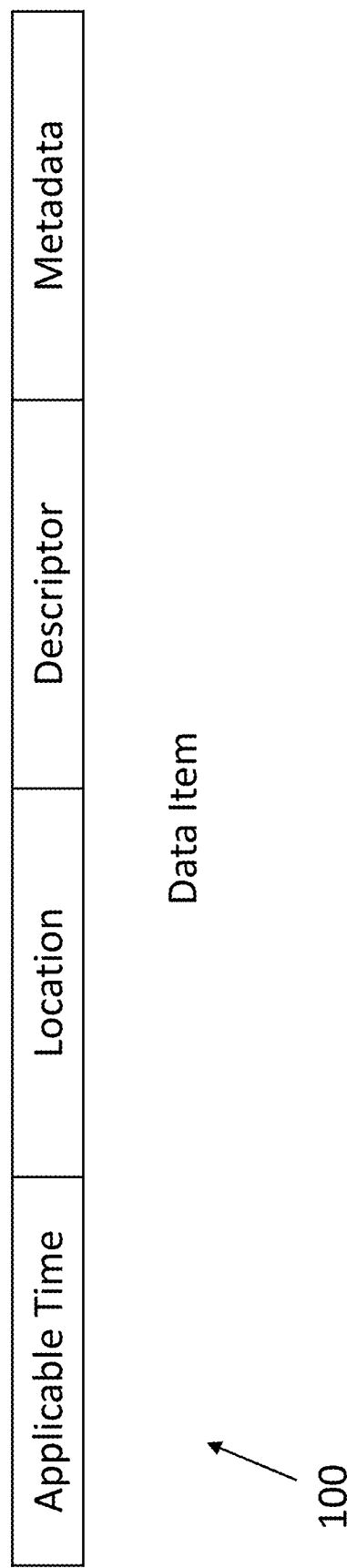
FIG. 1B is a schematic illustration of a data item associated with an event.

An example of a possible data item format is shown in FIG. 1B. The data item 100 exists in a standard format. The data item 100 comprises a descriptor of a feature. The descriptor may, for example, be an indication of the number of beds available in a hospital or an indication that a patient has been referred to a kidney specialist. In some cases, therefore, the descriptor comprises a value, e.g. the indication of the number of beds available, associated with a particular feature. In other cases, the descriptor does not provide a value associated with a feature, but simply indicates presence or absence of a feature, e.g. referral to a kidney specialist.

The data item 100 also includes a time associated with the feature. The time could indicate the time at which the number of beds indicated by the descriptor are available or a date on which the patient was referred to the kidney specialist. The data item 100 comprises a location associated with the feature. The location may be the hospital or ward on which the beds are available or the healthcare institution at which the referral was made.

For certain types of feature, a data item 100 may comprise metadata. For example, in the case that the data item 100 relates to a patient blood test result, the descriptor may comprise an indication of the type of test (e.g. HbA1c test) and a value indicating the numeric result of the test. The metadata may comprise an indication of the units of measurement, enabling the numeric result to be interpreted. Additionally or alternatively, the metadata may comprise an expected numeric range for a normal result for the patient.

Figure 2:
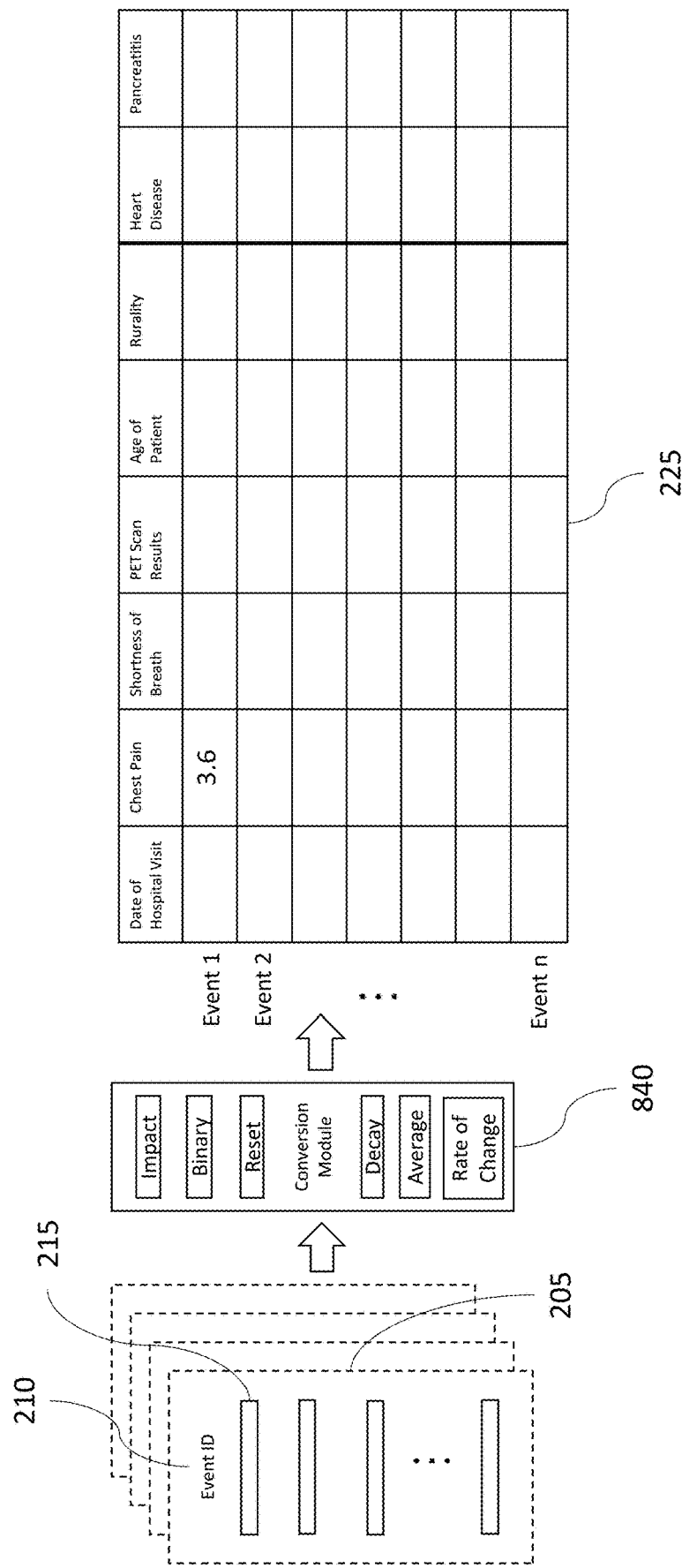
FIG. 2 is a schematic illustration of the process for producing a set of training data from sets of data items associated with events.

Reference is made to FIG. 2, which illustrates an example of how sets of data items, where each set of data items is associated with an event, may be used to generate training data for an artificial intelligence model, such as artificial intelligence model 865.

There is a set of data items for each event, for example set 205 of data items. The set 205 includes data items, such as data item 215. Each set of data items for an event is associated with an event identifier, such as an identifier of an event in which a patient presents at an accident and emergency department of a hospital. The event identifier 210 for set 205 of data items is shown in FIG. 2. The sets may be in the form of lists or any other kind of array. Each data item has a descriptor which describes a feature or indicator associated with the event, such as an event time, patient symptoms, patient history, treatment type, etc.

A conversion module 840 receives the sets of data items and generates from them, sets of training data for different models. An example set 225 of training data is shown in FIG. 2. Each training data set is organised in an array of columns and rows, each row being associated with a particular event, and each column being associated with a particular indicator or feature. It would be appreciated that any other organisation of the data structure may be utilised, but what is important is that each event may intersect with each particular feature or indicator. The conversion module 840 generates a score for each intersection. For example, in the training data set 225, in the intersection box of event 1 with chest pain, a score of 3.6 has been generated by the conversion module 840 and is inserted into the training data array. Each intersection of event and feature is assigned a particular score. One or more columns of the training data array 225 are reserved for labels for the model. In the example training data set 225 illustrated, the labels are heart disease and pancreatitis. The score in the heart disease column indicates whether or not the patient was diagnosed with heart disease. The score in the pancreatitis column indicates whether or not the patient was diagnosed with pancreatitis. The training data set shown may be a training data set that would be used for training a model for making a prediction of a possible disease for a patient that presents with chest pain at a hospital. This prediction is then used by the system to control allocation of medical resources for a patient. Although only two different diagnoses are shown in FIG. 2, in practice, there are likely to be a large number of different diagnoses possible for a patient presenting with the complaint of chest pain and, therefore, a large number of labels for the model. For example, the labels may also include bacterial or viral infection, pulmonary embolism, muscular pain, stable angina, myocardial infarction, anxiety attack, myocarditis, pericarditis, pneumonia, asthma, lung cancer, gastroesophageal reflux disease, and rib problems.

As noted, each row in the training data structure 225 is associated with an event. However, the same patient may be associated with multiple rows. For example, if a patient has had three hospital admissions, then there may be three rows for that patient in the training data set. Each row will contain scores representing administrative details of the admission—the date, the time, the length of stay, the admission source etc. Each row also contains scores representing the organisational state at the time of the admission—for example, the number of free beds and the number of patients waiting to be discharged. It also contains scores representing additional temporal data—e.g. the external weather data and the PM 2.5 pollution readings at the time. The row also contains scores representing features from the patient's medical record at the time of the admission—for example, their recorded diagnoses, laboratory test values, blood pressure readings etc. It also contains scores representing the patient's demographic data—e.g. marital status, deprivation score, ethnicity etc.

Once a training data structure, such as training data structure 225, has been produced, the training data structure is applied to train a machine learning model. The training data structure is applied to train a model in a supervised manner. For example, in the case that the model is a neural network, a backpropagation algorithm may be applied to adjust the weights associated with the connections between nodes of the network, so that the neural network reproduces the labels of the machine learning model from the training data. The trained machine learning model is produced by the system 800. The trained machine learning model may then be operated during an operating phase to produce outputs from operating phase data. The trained machine learning model may then be operating during the operating phase to produce outputs for controlling access to medical resources. Such a trained model may be operated by the machine learning system 40 shown in FIG. 1, which is used by a triaging system 10 to control access to medical resources.

The trained model takes an operating data set as an input, and produces an output in dependence upon this operating data set.

Figure 3:
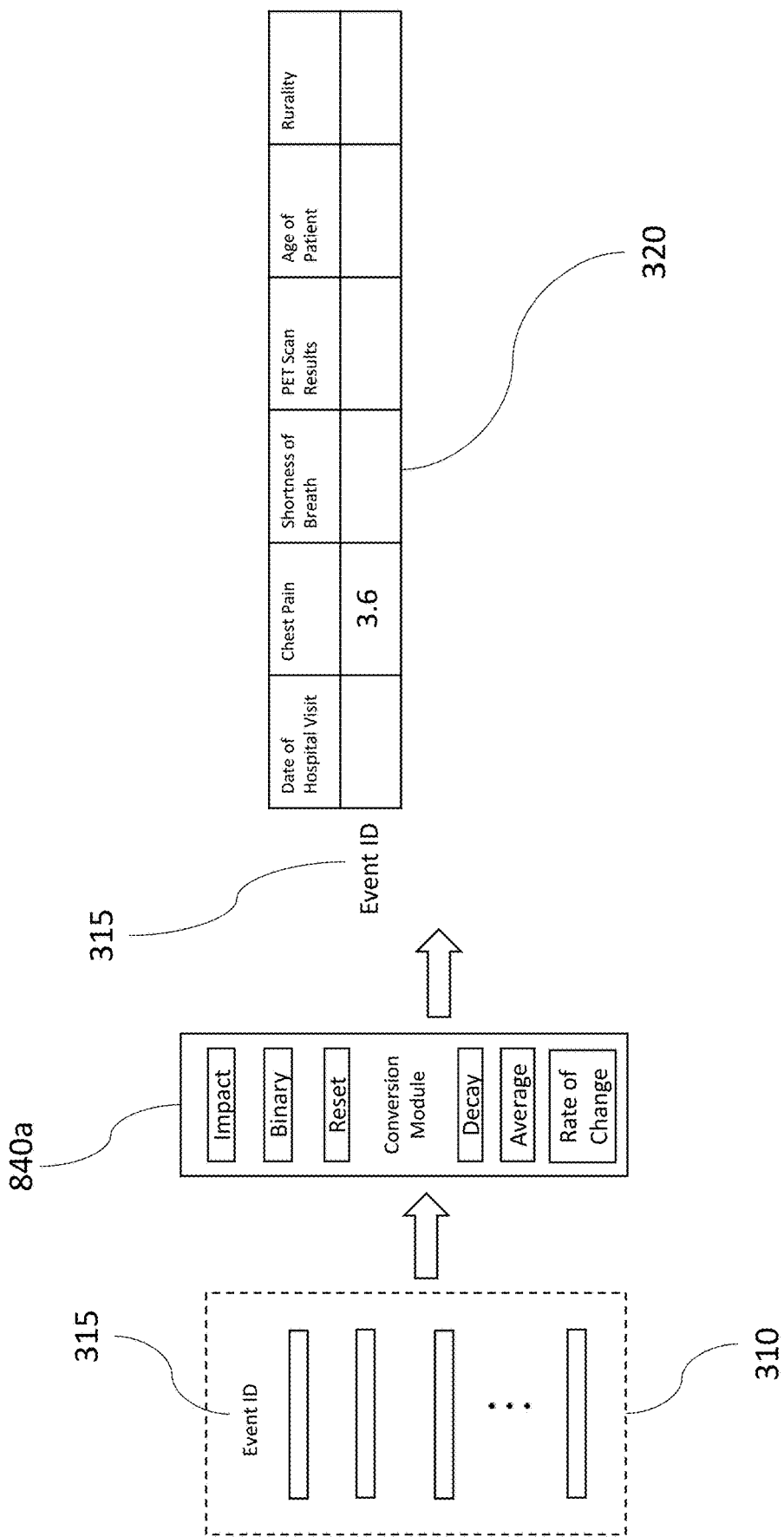
FIG. 3 is a schematic illustration of the process for producing a set of operating data from a set of data items associated with a patient.

Reference is made to FIG. 3, which illustrates an example of how a set 310 of data items associated with an event ID 315 is converted by the conversion module 840a into an operating data set 320 comprising a set of scores associated with each feature. The set 310 of data items comprises data items that are derived from the initial event data associated with the event. The set of data items 310 also comprises additional data, such as data from patient health records. Each of the set of data items 310 includes a descriptor related to a feature or indicator. Some descriptors comprise initial event information, such as a time of the event, whilst other descriptors comprise patient health data, such as symptoms and diagnoses associated with that patient. The conversion module 840a receives the set of data items 310 and outputs the operating data set 320 determined in dependence upon the set of data items 310. The example operating data set 320 shown in FIG. 3 corresponds to the training data set 225 shown in FIG. 2. In other words, the operating data set 320 is for use as an input, during the operating phase, to the model trained by the training data set 225 during the training phase.

The operating data set 320 comprises scores associated with a plurality of features. A score may be determined in dependence upon the number of times in the set of data items 310, a descriptor indicating that feature appears. E.g. a score associated with a patient symptom may be higher if descriptors of that feature appear more frequently in the set 310 of data items. The score for a feature may be determined in dependence upon the time associated with a particular data item recorded in the set 310 of data items, e.g. the time at which a symptom applied to the patient.

Unlike a training data set, an operating data set does not include labels for the models. As shown in the example of FIG. 3, the example of an operating data set 320 that is shown does not include the indications of whether or not the patient had certain diseases (i.e. heart disease and pancreatitis) in the corresponding training data set 225 illustrated in FIG. 2. Instead, in the operating phase, the output from the model is used to determine the probability of the patient having each of these diseases. An output of 1 from a first node of the model indicates that the patient certainly has heart disease, whilst an output of 0 from the first node of the model indicates that the patient certainly does not have heart disease. Numbers between 0 and 1 provide an indication of the probability that the patient has heart disease. Similarly, an output of 1 from a second node of the model indicates that the patient certainly has pancreatitis, whilst an output of 0 from the second node of the model indicates that the patient certainly does not have pancreatitis. Numbers between 0 and 1 provide an indication of the probability that the patient has pancreatitis.

Therefore, it is understood that for a range of different possible diagnoses, the output provides a possible probability associated with each diagnosis. These probabilities are used to control access to medical resources, by selecting the medical resource (e.g. CT scan or a microbiology test) for confirming or refuting the most likely diagnosis indicated by the model. For example, if the output from the model trained using the training data set 225 indicates that the patient has a higher probability of heart disease than of pancreatitis, the system may generate a request for a CT scan. On the other hand, if the output from the model trained using the training data set 225 indicates that the patient has a higher probability of pancreatitis than heart disease, then the system may generate a request for a microbiology. Heart disease and pancreatitis are examples, but different models may be applied to generate other outputs suggesting a need for certain medical resources.

The outputs from the machine learning models discussed may also be applied to perform treatment planning, and to control treatment and diagnosis. For example, one or more machine learning models may be applied to determine how long an inpatient is likely to stay in hospital for. One or more machine learning models may also be applied to predict the resources or staff that are likely to be used by the patient. Such predictions can be used to perform treatment planning. The predictions may be used to select a treatment option for a patient, depending upon the patient's predicted use of medical resources.

The techniques described herein may be applied to train and operate machine learning models to determine outputs other than values predicting access to medical resources. These outputs may then be applied by the system to select treatment and diagnosis options.

Medical resources in this context may be understood to be services and equipment that can be used for providing healthcare for a patient. These include outpatient appointments, clinical assessment, nursing care, diagnostic tests, examinations and medical equipment. The medical resources may be used to perform medical treatment or diagnosis. Examples of medical treatments include prescriptions of medicines, prescriptions of medical aids, patient education, immunisation, radiotherapy, and surgery. The medical treatment and diagnosis is administered by healthcare institutions, such as clinics, general practices, acute hospitals, urgent care centres, trauma centres, and specialist medical facilities.

As an example, one or more machine learning models, may be applied to determine estimates for waiting times for different types of medical resource. Such outputs may be used to control treatment or diagnosis for patients. For example, a machine learning model may output likely waiting times for a patient to access a gastric specialist and a kidney specialist. These output waiting times may be processed by the system to obtain a recommendation as to which specialist the patient should see. Hence, different types of machine learning model can be trained and applied for use in performing treatment planning.

As another example, one or more machine learning models may be applied to select between different types for scan, e.g. MRI or CT, for patients. A model may directly output a score associated with MRI and a score associated with CT. CT scans are cheaper, more comfortable and better for some conditions. MRI does not require the same exposure to ionising radiation, but is more expensive and can be difficult for some patients to undertake.

The machine learning system 40 or terminal 25 shown in FIG. 1, produces treatment recommendations from the output of machine learning models by post-processing output values from the models. In this case, the post-processing comprises generating a treatment recommendation based on the output values for the models. Following the example described above of the kidney and gastric specialist, in response to receiving from the models, output values representing likely waiting times for both a gastric specialist and a kidney specialist, these output values are post-processed to obtain a recommendation as to which specialist the patient should see (i.e. the one with the shorter waiting time). The recommendation as to which specialist is used to control access to medical resources. The system 40 or terminal 25 books an appointment with the specialist in accordance with the recommendation, thereby performing an assignment of medical resources.

Different data sets may be provided to multiple machine learning models and the outputs used from those multiple models used to assign medical resources. As an example, the predicted use of resources output by a machine learning model may be post-processed in combination with the urgency of patients output by another machine learning model. The result of this post-processing may be used to provide treatment recommendations so as to prioritise certain patients, with more urgent patients requiring fewer medical resources being given priority. For example, a first machine learning model may predict waiting times (e.g. depending upon relevant staff available) for access to a particular medical resources, whilst a second machine learning model may predict the probability that a patient has a particular condition. The outputs are used together by the system to control the patient's access to the medical resources. The system is more likely to give the patient access to the resource if the resource has a high availability, e.g. waiting times are short, and the patient has a high probability of having a relevant condition requiring access to the resource. The system is less likely to be give the patient access to the resource if the resource has a low availability, e.g. waiting times are long, and the patient has a low probability of having a relevant condition requiring access to the resource. The relevant condition may be chest pain, with the medical resource being a CT scan.

In some cases, the assignment of medical resources for a patient may depend upon model outputs relating to other patients. For example, the selected one or more models may be run by the system to obtain a result reflecting the value of a particular medical resource for a patient. Such model/s may be applied to data associated with a plurality of patients in order to determine the value of the particular medical resource for each patient. Post processing is then carried out by the system in order to assign the medical resource to one or more of the patients in dependence upon the value that the medical resource holds for each of the patients. In effect, the assignment of the resource is carried out based on the priority of each patient, as indicated by the one or more models. For example, a model may be run for a patient that outputs an indication of the value of a CT scan for that patient. For example, the model may output an indication that a CT scan of a patient's heart is highly recommend given the patient's report of chest pain and family history of heart disease. The system collects model outputs for a plurality of patients, each output indicating the value that the CT scan holds for each patient. The system post-processes the outputs indicating the value of the CT scan for each patient and assigns a CT scan to be carried out for a subset of the patients for which the outputs indicate that a CT scan has the highest value. Therefore, the CT scan resources are assigned to those patients having the highest priority.

In some cases, the system of prioritising the patient's access to medical recourses based on the value of those resources to patients may take into account alternative options available to a patient. If there are alternative medical resources that could be assigned to a patient, the patient may be assigned the alternative medical resource that has less value for them. For example, a first model may be run to determine the value of a CT scan for a patient. A second model may be run to determine the value of an MRI scan for a patient. Post-processing is then carried out to assign either a CT scan or an MRI scan for a patient. Even if the CT scan is a preferential test when compared to an MRI scan, the MRI scan may be assigned for the patient if the CT scan resources are in high demand by other patients.

In some cases, patients may have a higher priority of access to the CT scan due to an absence of alternative test options (e.g. MRI scanning). For example, the system may run a CT model that outputs an indication that a CT scan would provide a high level of value for diagnosing a first patient, whilst outputting a moderate level of value for diagnosing a second patient. The system may also run an MRI model that outputs an indication that an MRI scan would provide a moderate level of value for diagnosing a first patient, whilst outputting an indication of no value for diagnosing a second patient. The system then performs post-processing in dependence upon these indications and assigns the CT scan resources for the second patient, despite them providing lower value for diagnosis for the second patient than for the first patient, since the second patient does not have the MRI scan as a viable alternative. The system assigns the MRI scan resources for the first patient, despite the CT scan providing higher value for the first patient because, unlike for the second patient, the MRI scan is a viable alternative to the CT scan.

Therefore, the models can be used to determine the value of different medical resources for different patients so as to assign resources to patients in dependence upon the priority of access of those patients to those resources.

Figure 2A:
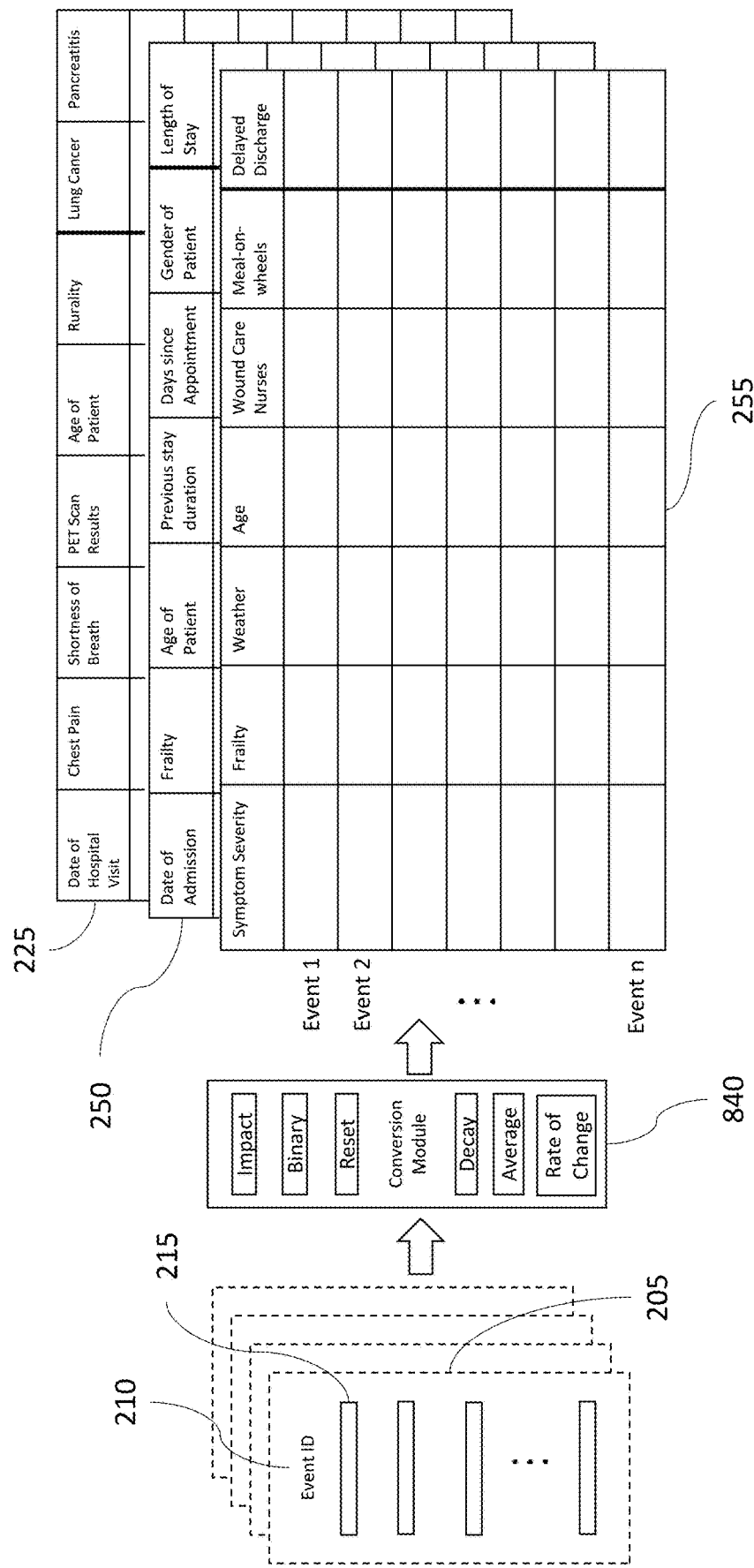
FIG. 2A is a schematic illustration of the process for producing different sets of training data for training different machine learning models.

Reference is made to FIG. 2A, which illustrates different training data structures that could be produced for training machine learning models. Like elements to those in FIG. 2 are referenced using the same reference numerals.

Models may be generated for making many different types of determination, each model using a different training data structure. FIG. 2A shows further examples of other training data structures that can be generated from sets of data items associated with events.

The example training data structures include a training data structure 255 for training a model for determining the probability of a patient's discharge from hospital being delayed. The system would run this model at the time of the patient's admission into the hospital. The relevant 'event' for each row of the training data structure is, therefore, an admission of the patient into hospital. Delayed discharges are very frequently due to problems with the availability of resources for the patient in community care and social care. For example, a patient may not be able to be discharged until community nurse visits for wound care have been scheduled and their social care requirements (e.g. meal-on-wheels) have been restarted, following their stay in hospital. Suitable features or indicators (those having predictive value for determining a delayed discharge) are retrieved and added to the sets of data items, which are then used to generate scores for the training data structure for this model. As can be seen in the training data structure, two of the features used to train the model are the availability of wound care nurses, and the availability of meal-on-wheels. Early prediction of a delayed discharge allows control to be made over appropriate medical resources, such as the allocation of patients to hospital beds.

In this case, the label column is populated with binary information (1 or 0) indicating whether or not a delayed discharge occurred for the patient that was admitted to hospital.

Also, shown in FIG. 2A is a training data structure 250 for training a model to predict the length of stay for a patient for a patient admitted to hospital. The model in this case is a regression model. The length-of-stay is the time between admission and discharge. A long length-of-stay for a patient is often associated with poor health outcomes including, for example, mortality and risk of nosocomial infection. Prediction of long length-of-stay allows the system to assign access to appropriate medical resources early in their admission. For example, a long length of stay may indicate that a patient needs early access to a multi-disciplinary team (MDT), comprised of staff from a range of clinical specialties. This team will then address the patient's clinical needs as quickly and comprehensively as possible.

Suitable features or indicators (those having predictive value for determining a length of stay, such as previous stay duration during a hospital admission or frailty of patient) are retrieved and added to the sets of data items, which are then used by the conversion module 840 to generate scores for the training data structure 250 for this model. In the training data set 250, the label column is populated with a value indicating the length of stay of the patient.

Also shown in FIG. 2A is the training data structure 225 that is discussed above with respect to FIG. 2. As described above, this training data structure 225 is used to train a model for determining the probability that a patient has heart disease and the probability that a patient has pancreatitis.

The model that is trained using the training data structure 225 may be used to select an order set. An order set is a group of related orders which a physician can place with a few keystrokes or mouse clicks in a clinical information system. An order set allows users to issue pre-packaged groups of orders that apply to certain diseases/disorders. These orders can cover almost all healthcare resources or treatments. Most frequently, however, the orders relate to specific laboratory tests, radiology tests, or prescribed medication.

The system uses the model trained using training data structure 225 described above to classify the most likely set of potential diagnoses for a given patient. It subsequently identifies the most appropriate order sets to request for the patient in dependence upon the most likely set of potential diagnoses. The system may use other models than that trained using the training data structure 225. The system may use a number of deep learning classification models that predict which order sets should be requested for a patient. The system may make a determination of the order set to be requested for a patient upon their admission to a healthcare institution.

The assignment of order sets by the system is patient specific. The system may assign orders sets to patients with the same presenting complaint differently, based on data items derived from their health records. For example, different patients presenting with chest pain may have different order sets assigned—if the algorithm determines that a patient has a high-risk of heart disease (e.g. using the model trained using training data structure 225), then the order set will include a CT scan. This scan—which is costly and not without risk—would not be ordered for a patient with a low heart disease risk.

To assign an order set for a patient, the system may apply an iterative process. The initial output of a first machine learning model is used to generate an appropriate assignment of an order set for the patient. Part of the order set contains the tests required to confirm or reject the potential diagnosis made by the first machine learning model. At a later time, the results of these ordered tests become available for review. If the potential diagnosis output by the first model is confirmed, an appropriate treatment is assigned for the patient. On the other hand, if the initial diagnoses are rejected on the basis of the test results, the operating data structure input to the model is expanded to include at least one score representing the test results. This operating data structure is input to a second machine learning model. The second machine learning differs from the first machine learning model in that it includes at least one additional input node for receiving the at least one score representing the test results and in that it does not have the output node representing the initial potential diagnosis made by the first machine learning model. By running the second machine learning model a new potential diagnosis can be obtained, which may then be used to assign medical resources for treatment or diagnosis.

As an example, a patient may present in hospital with recent onset of chest pain. A model supervisor selects the most general deep-learning model for this presenting complaint. This model has all possible classification output nodes for chest pain. The possible output nodes for the model may represent: bacterial or viral infection, pulmonary embolism, muscular pain, heart disease, stable angina, myocardial infarction, anxiety attack, myocarditis, pericarditis, pneumonia, asthma, gastroesophageal reflux disease, and pancreatitis and rib problems.

In response to input of an appropriate set of values from an operating data set, the model outputs a set of values, each indicating the likelihood for each diagnostic classification. The set of values indicate that angina is the most likely diagnostic classification. In dependence upon the set of values, the system, therefore, suggests the appropriate order set for the patient—in this case an ECG test, a CT coronary angiography, and certain laboratory blood tests. Once all of these tests have been performed, the test results indicate that the patient does not have angina.

The model supervisor then selects a second model. The operating data set that was input to the first model is updated to include the new blood tests results from the tests that have been performed. In this case, the second model is for the same presenting complaint—chest pain—but includes an input node for receiving a score associated with the new blood test results. The second model also lacks the output node associated with the angina diagnosis since this diagnosis has already been ruled out clinically. The second model then runs on the updated data set and outputs a set of values indicating that the most likely diagnosis is a bacterial or viral infection. In response to this determination, the system outputs an instruction for further testing, such as further blood test and a chest x-ray.

This process of using different models and ordering tests then continues iteratively until the diagnosis is determined.

Other than the controlling of order sets, a further way in which a model that provides potential diagnoses (such as that produced using training data structure 225) may be used is in the triaging of patients. In this case, based on the patient-level data and the presenting complaint, a model outputs a set of values indicating a set of potential diagnoses for different diseases. Based on the probabilities for these diagnoses, the system triages patients into different categories, making sure that the patients who require immediate access to resources and treatment get it.

For example, a model can output values indicating the risk level of a patient for both sepsis and acute kidney injury (AKI). In both cases, these patients need to be triaged extremely quickly and put on treatment as soon as possible. In the case of sepsis, patients need to be administered with courses of broad spectrum antibiotics (e.g. ceftriaxone, azithromycin, ciprofloxacin, vancomycin, and piperacillin-tazobactam). In the case of AKI, patients may need immediate intravenous fluid therapy, antibiotics, and certain medications stopping. The system outputs an indication of the treatment to be applied in each case in dependence upon the risk level.

In each of the example training data structures 225, 250, 255 shown in FIG. 2A, different features for which scores are provided are shown. For example, in the training data structure 250 for the length of stay model, scores for frailty of the patient are provided. Such scores are not provided in the training data structure 225 for the disease diagnosis model, but scores for chest pain are instead provided. Therefore, in some embodiments, different features are scored in the different training data sets. However, in other example embodiments of this application, the set of features that are scored in the different training data structures may be the same, with only the selected labels (e.g. "length of stay", "Delayed Discharge", "Heart Disease" and "Pancreatitis") being different between the training data sets.

For each of the training data sets shown in FIG. 2A, the data items for producing the respective training data set may comprise descriptors indicating any of the features listed above for producing the training data set 225.

Figure 3A:
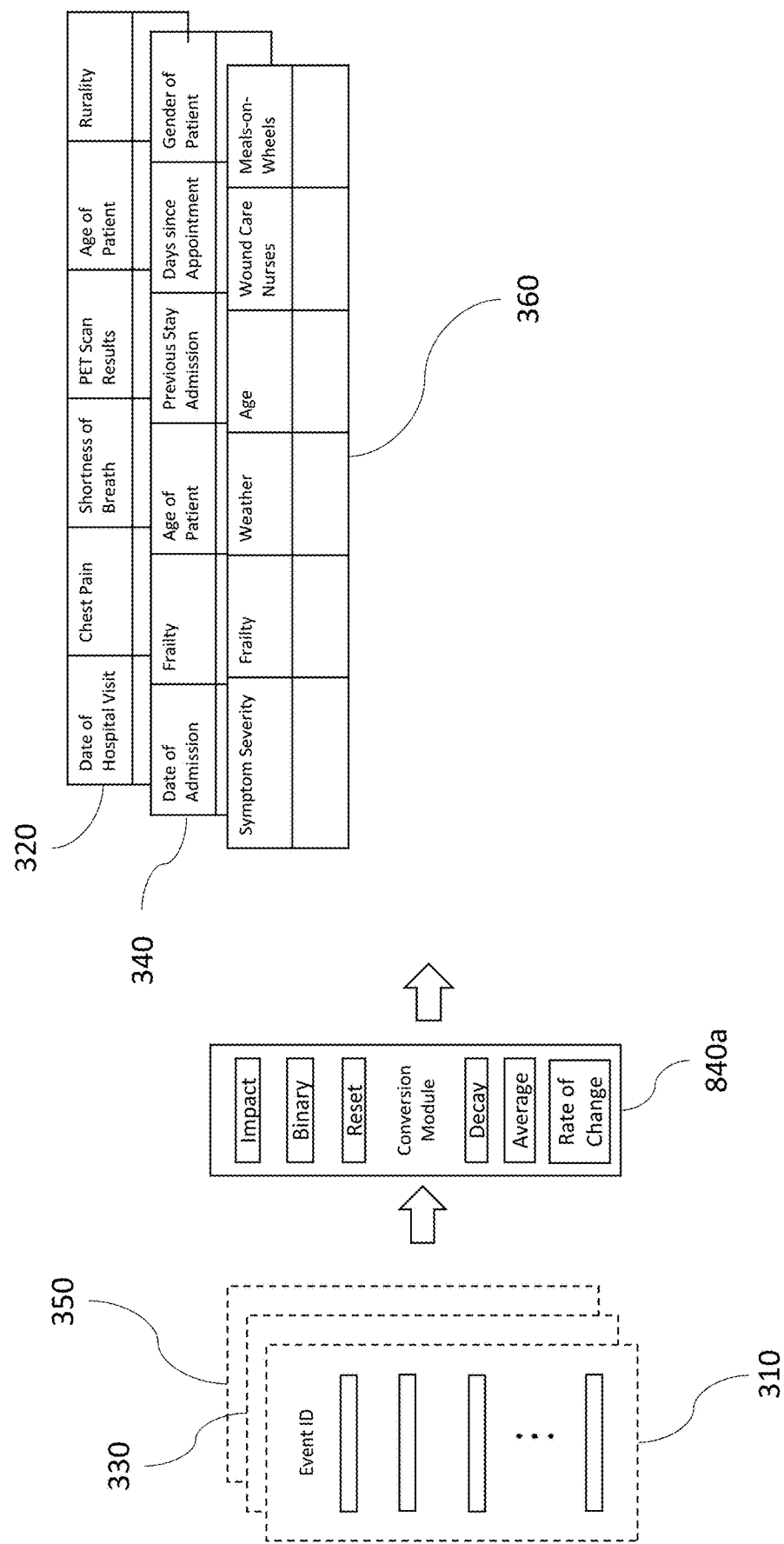
FIG. 3A is a schematic illustration of the process for producing different sets of operating data for input to different machine learning models during an operating phase.

Reference is made to FIG. 3A, which shows operating data sets corresponding to the training data sets shown in FIG. 2A that are generated by the conversion module 840. Like elements to those in FIG. 3 are referenced with like reference numerals. FIG. 3A illustrates how a set 330 of data items is processed by the conversion module 840a to produce the operating data set 340. This operating data set 340 is used as an input to the model trained by the training data set 250 to obtain an estimate of the length of stay that will be required of a patient. FIG. 3A also shows how a set 350 of data items is processed by the conversion module 840a to produce the operating data set 360. This operating data set 360 is used as an input to the model trained by the training data set 255 to obtain the probability that a delayed discharge will occur for the hospital admission.

For each of the training data sets shown in FIG. 3A, the data items for producing the respective training data set may comprise descriptors indicating any of the features listed above in set of data items 310 for producing the operating data set 320.

The conversion module 840a may perform the same function transformations to produce the operating data set feature scores (without producing the labels) as performed by the conversion module 840 when producing the equivalent training data set feature scores.

Figure 10:
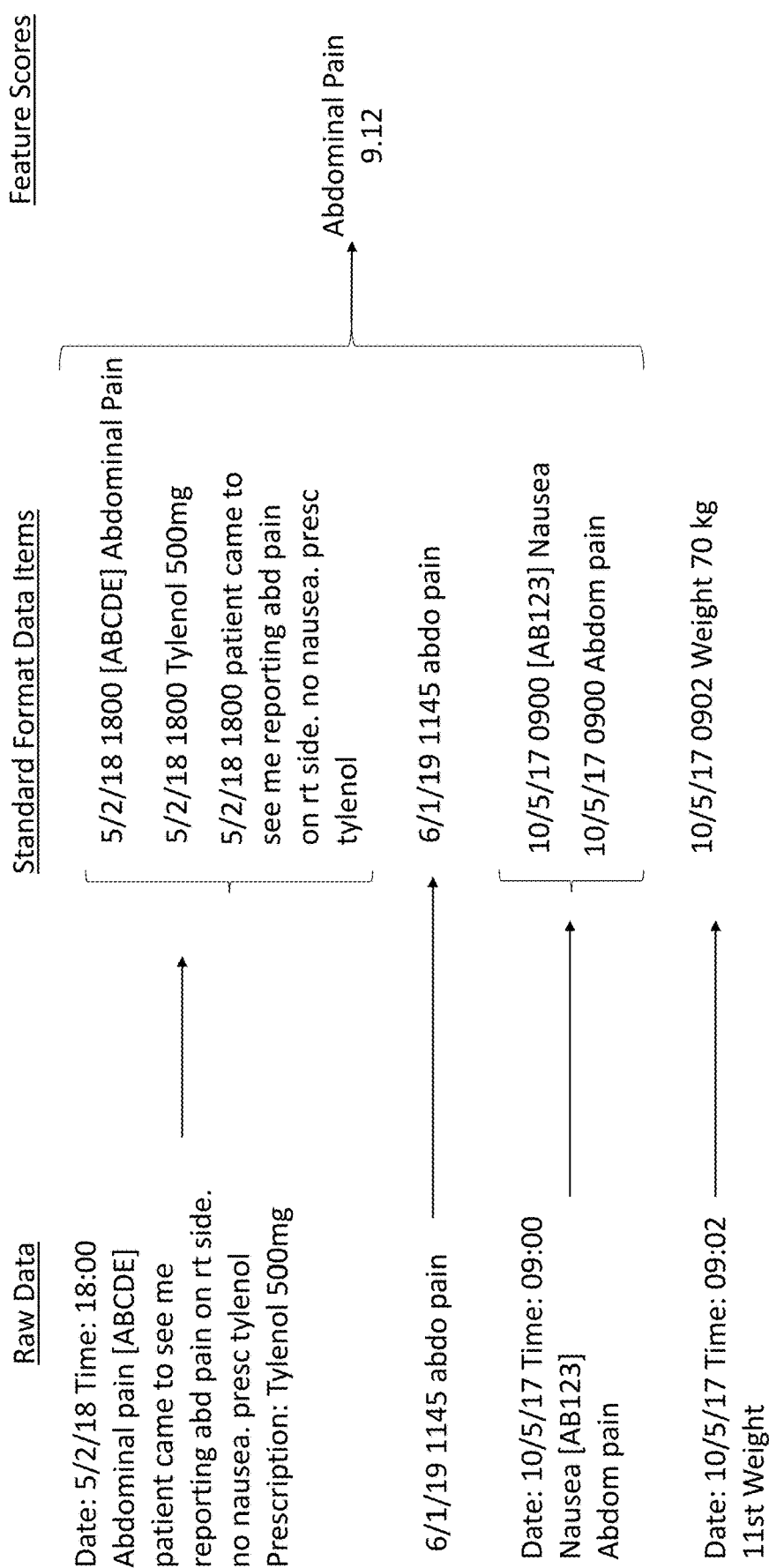
FIG. 10 illustrates an example of the calculation of feature scores from raw data.

Reference is made to FIG. 10, which illustrates an example of how a feature score, which can be included in the training and operating data sets, is produced from raw data. Specifically, FIG. 10 illustrates an example of producing a feature score relating to abdominal pain. A set of raw data items relating to a patient's health status is shown in this example. This raw data represents information about a patient that may be extracted from one or more health records of a patient, or obtained from an app in the client device, for example.

The raw data may exist in several different formats. The raw data may include encoded data (e.g. a 5 byte code or 18-digit integer) used to encode patient health records across the health service. The raw data may include, or may be wholly, free text. The raw data may include a numeric value for a measurement described by the coded or free text label. Each item of raw data then comprises at least a coded or non-coded descriptive label. Each item of raw data includes a timestamp indicating its time of recordal. At least some items of raw data may separately indicate a time indicating when the descriptor applied.

A pre-processing stage (which is shown as S310 in FIG. 7, which is discussed in more detail below) is performed by the system, and involves producing a set of data items in the standard format from the raw data. The standard format may include descriptors of features comprising a coded format (e.g. the standard 5 byte code) and/or comprising free text. The raw data may include data items in the standard format, and so, for these data items, no conversion to the standard format takes place. For example, as shown in FIG. 10, the raw data includes information recording that abdominal pain was reported on 6 Jan. 2019. This information may be stored in the patient record as a data item in the standard format. When the whole data set is placed in the standard format, a copy of this data item is stored as part of the standard format data, without being converted to a different format.

Some of the raw data may not be in the standard format, but can be mapped to one or more data items in the standard format. This record in the raw data may be used to produce a plurality of data items in the standard format. As shown in FIG. 10, the raw data from a patient's record contains encoded information recording that the patient had abdominal pain on the 5 Feb. 2018. The same record on 5 Feb. 2018 also contains an encoded data item indicating that Tylenol was prescribed. The same record on 5 Feb. 2018 also contains free text describing the patient symptom of pain in the right side and indicating Tylenol was prescribed. From this raw data, three different data items in the standard format are produced by the system. Each of these standard format data items is used by the conversion module to determine the score for the feature 'abdominal pain'.

The raw data shown in FIG. 10 further includes a record of "abdo pain" made on 6 Jan. 2019 and a record of "Abdom pain" made on 10 May 2019. These records are both placed into the set of data items in the standard format with a date and time at which the indicated feature was applicable and the relevant coded or free text information. The record of the weight made on 10 May 2019 has also been converted during pre-processing to be in the standard format from the raw format.

Once a set of data items from a patient's records has been extracted and converted to a set of items in the standard format, feature extraction (S315a or S315b in FIG. 7) is then performed by the conversion module to produce scores to be input to a machine learning model (e.g. a neural network or decision tree). In the example shown in FIG. 10, all of the data items in the standard format, with the exception of weight (which is not relevant to the feature 'Abdominal pain') are used to determine the score associated with the feature 'Abdominal Pain'. The score provides an indication of the impact of the feature and may, but not exclusively, represent the severity of the symptom. The score is provided to the machine learning model as an input when evaluating a result (e.g. patient outcome, diagnosis) for a patient.

When determining a feature score in dependence upon the data items, different transformations may be applied to determine the feature scores in dependence upon the data items. The transformations may vary between models, with different transformations being applied to determine scores associated with different model. The transformations may vary for different types of features score, with different transformations being applied to different data items.

In some examples, the score for a feature is determined in dependence upon a single data item. For example, the time of admission of a patient into a hospital provided in a data item, may be used by the conversion module to produce a feature score representing this time. However, in other cases, the score that is assigned to a particular feature may be determined in dependence upon the number of times that the relevant data items appear in the set of data items. For example, in the example of FIG. 10, the score assigned for abdominal pain may be higher due to multiple data items indicating abdominal pain that are present in the standard format data.

Although the score for certain features may be dependent upon the number of times that certain data items appear in the set of data items, there may be certain limitations upon the counting of data items when determining the score. Specifically, the score that is calculated in dependence upon the number of data items depends upon whether a plurality of the data items were recorded within a certain time window. If a plurality of data items were recorded within a predefined time window, those plurality of data items are counted as being a single data item for the purposes of determining the feature score. The time windows repeat sequentially one after the other.

In an example, a time period of one day may be defined for calculating a score associated with abdominal pain. A plurality of sequential time windows of one day are defined. Any data items indicating abdominal pain that fall within a particular one day time window are treated as a single data item for the purposes of determining the feature score.

Another way in which the score that is assigned to a particular feature may depend upon the applicable time associated with the data items is through the use of a decay function. For example, when determining a score, more weight may be given to records that were made more recently or for which the applicable time is more recent. For example, when determining the score to be assigned for chest pain, the information that chest pain was recorded on 5 Feb. 2018, may be given more weight than the information that chest pain was recorded on 10 May 2017. The calculation of the score is performed using rule based operations executed by the conversion module. The rules may be based on mathematical functions, for example linear or sigmoid. Parameters for the rules can be adjusted (gradient, minimum/maximums, coefficients) during the optimisation phase (S340 in FIG. 7). For example, the contribution to a score for chest pain may be adjusted to approach zero as the time elapsed since a data item indicating chest pain approaches 2 years.

Another way of generating the score is to use a binary score for indicators which are either present or not present. For example, a family history of the particular disease is scored by 1 or 0 for a patient, regardless of the number of times a family history of the disease appears in the set of data items for that patient. For example, a person either has a family history of heart disease or they do not, and a score associated with a family history of heart disease will be set to either 1 or 0.

Another technique for generating a score that is performed by the conversion module is to determine the score in dependence upon the rate of change of a numeric value indicating by a series of data items. For example, the conversion module may determine a score indicating the rate of change of a patient's health condition in dependence a plurality of data items, each comprising a descriptor for that health condition.

Another way of generating a score is to generate an average of values which have been reported over a time period. For example, if a column in the training data set relates to smoking, and the patient has reported different number of cigarettes being smoked per day at different times in their history, an aggregate number can be recorded as the score. The aggregate number could, for example, be an average or a mean, or any other statistical representation of the individually reported numbers. One possibility is a rolling mean of previously collected values. Such a rolling mean may be applied to determine a score associated with blood test values.

The conversion module also applies categorisation to determine the scores for a particular patient. For example, each data item may be placed into a category depending upon a value for a feature that it represents. A statistical operation (e.g. averaging or determining standard deviation) is then performed to the categorisation values to obtain a score for the feature. A numeric value is associated with each category and is assigned for each data item in that category. The average of the numeric values for each data item is determined and used to provide a score for a patient. The standard deviation of the determined numeric values may also be determined and used for determining the score for the patient.

In some cases, as mentioned, the data items may comprise metadata. For example, a data item representing a blood test measurement may comprise an indication of the units of measurement. The conversion module calculate the features scores in dependence upon this metadata. For example, the conversion module may interpret the descriptor (e.g. containing a blood test result) using the metadata (e.g. the unit of measurement for the blood test result).

The following description provides an example explanation of machine learning processes that may be used to implement embodiments of the application. Furthermore, a description of the hardware in which embodiments may be implemented is provided.

Machine Learning is a branch of research for enabling computer systems to solve problems and perform tasks without explicit instructions. Machine learning systems autonomously analyse data sets, referred to as 'training data', in order to train mathematical models during a training phase. Once trained on the basis of the training data, the mathematical model is then applied to data sets to make predictions and/or decisions during an operating phase.

There are two distinct types of machine learning, referred to as supervised learning and unsupervised learning. In supervised learning, the training data for constructing the model includes both input data and desired output data. The parameters of the model are tuned on the basis of the input data so as to result in a model that is able to approximately generate the output data from the input data. The output data typically comprises a set of labels that have been provided by humans to label the sets of input data.

Supervised learning may be used to perform classification of input data into a particular category. For example, a mathematical model that is trained to perform optical character recognition may, when provided with data representing an image of a letter of the alphabet, output an indication of the one of the 26 different letters of the alphabet that is shown in the image. This type of model is referred to as a classifier model, since the image is classified into one of a set of categories (i.e. letters of the alphabet). Another type of supervised learning model may be used to perform regression analysis of input data. In this case, the output data comprises one or more continuous values rather than a discrete class. For example, a mathematical model may be trained to output an estimate for the value of a property given a set of input data, including location, size, age, etc.

In unsupervised learning, the training data for constructing the model includes input data, but does not include labels or outputs of the model. Instead of training the model to reproduce the output data from the input data, in unsupervised learning, the model is trained on the basis of commonalities in the training data and provides outputs based on the presence or absence of those commonalities in the future input data. Unsupervised learning has applications in dimensionality reduction and in cluster analysis.

One type of model widely used in the field of machine learning is the artificial neural network. Neural networks comprise arrangements of sets of nodes which are interconnected by links and which interact with each other. The principles of neural networks in computing are based on information about how electrical stimuli convey information in the human brain. For this reason, the nodes are often referred to as neurons. They may also be referred to as vertices. The links are sometimes referred to as edges. The network can take input data and certain nodes perform operations on the data. The result of these operations is passed to other nodes. The output of each node is referred to as its activation or node value. Each link is associated with a weight. A weight defines the connectivity between nodes of the neural network. Many different techniques are known by which neural networks are capable of learning, which takes place by altering values of the weights.

Figure 5:
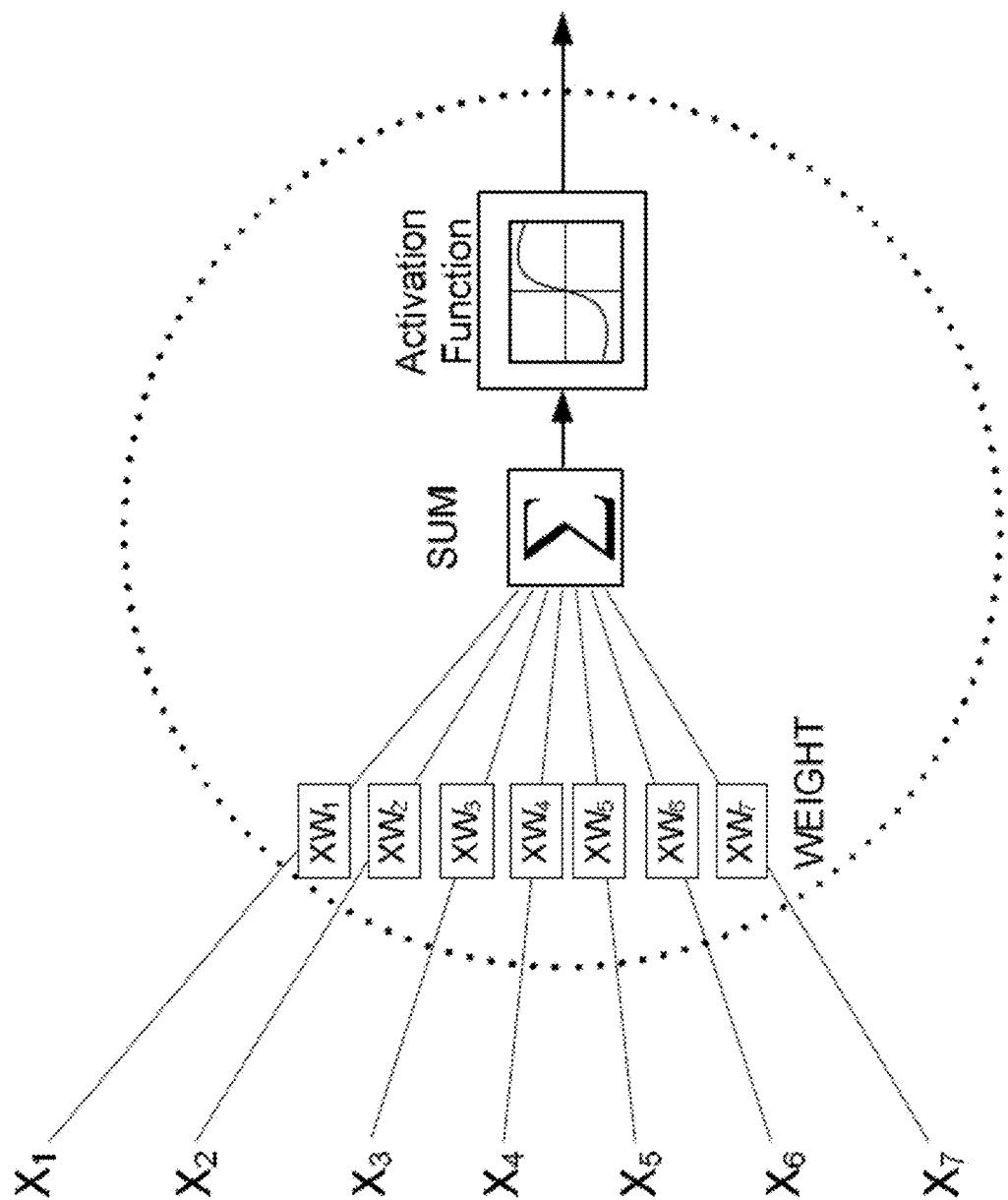
FIG. 5 is a simplified schematic view of a neuron.

FIG. 4 shows an extremely simplified version of one arrangement of nodes in a neural network. This type of arrangement is often used in learning or training and comprises an input layer of nodes, a hidden layer of nodes and an output layer of nodes. In reality, there will be many nodes in each layer, and nowadays there may be more than one layer per section. Each node of the input layer Ni is capable of producing at its output an activation or node value which is generated by carrying out a function on data provided to that node. A vector of node values from the input layer is scaled by a vector of respective weights at the input of each node in the hidden layer, each weight defining the connectivity of that particular node with its connected node in the hidden layer. In practice, networks may have millions of nodes and be connected multi-dimensionally, so the vector is more often a tensor. The weights applied at the inputs of the node Nh are labelled w0 . . . w2. Each node in the input layer is connected at least initially to each node in the hidden layer. Each node in the hidden layer can perform an activation function on the data which is provided to them and can generate similarly an output vector which is supplied to each of the nodes No in the output layer No. Each node weights its incoming data, for example by carrying out the dot product of the input activations of the node and its unique weights for the respective incoming links. It then performs an activation function on the weighted data. The activation function can be for example a sigmoid. See FIG. 5. The network learns by operating on data input at the input layer, assigning weights to the activations from each node and acting on the data input to each node in the hidden layer (by weighting it and performing the activation function). Thus, the nodes in the hidden layer operate on the weighted data and supply outputs to the nodes in the output layer. Nodes of the output layer may also assign weights. Each weight is characterised by a respective error value. Moreover, each node may be associated with an error condition. The error condition at each node gives a measure of whether the error in the weight of the node falls below a certain level or degree of acceptability. There are different learning approaches, but in each case there is a forward propagation through the network from left to right in FIG. 4, a calculation of overall error, and a backward propagation from right to left in FIG. 4 through the network of the error. In the next cycle, each node takes into account the back-propagated error and produces a revised set of weights. In this way, the network can be trained to perform its desired operation.

Different types of neural network are known. One type of neural network is a feedforward neural network, in which the information in the network travels through the network in only one direction from the input layer to the output layer. In each case, the activation of the next layer depends upon the activation of the previous layer and the weights of the connections between the two layers. Feed forward neural networks can be time aware, in which case, the activation of a particular node is dependent upon time values associated with the input data. Another type of neural network is a recurrent neural network, in which, outputs from nodes of the neural networks are provided as inputs to earlier nodes in the neural network. This may be performed by providing the outputs of the neural network as inputs to the neural network. Alternatively, this may be performed by nodes in the hidden layer/s of the network receiving as inputs, their previous output from one or more iterations prior to their current iteration. A special type of recurrent neural network is a Long Short Term Memory (LSTM) neural network, in which nodes retain information for longer periods of time and are, therefore, capable of processing data having time gaps.

Figure 6:
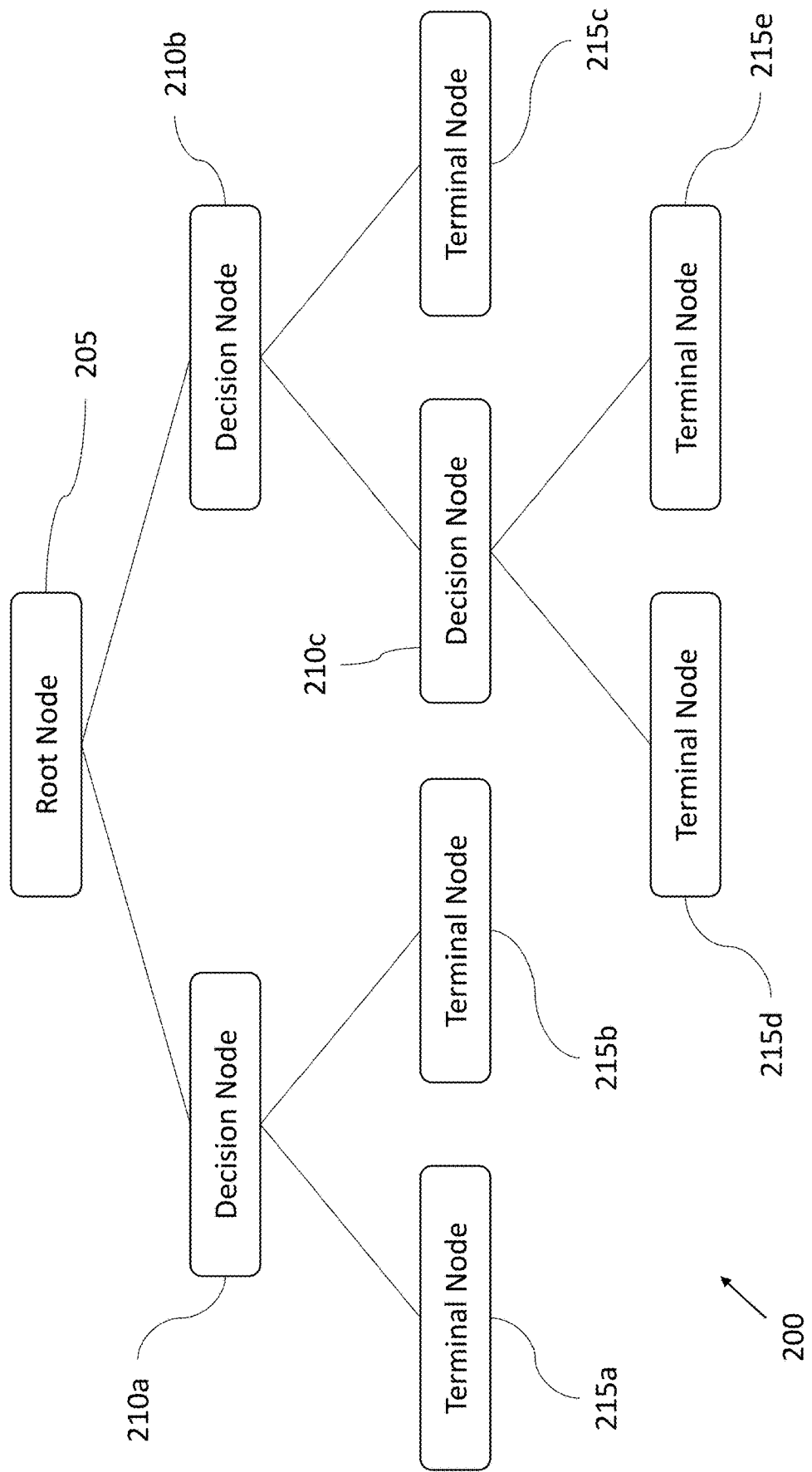
FIG. 6 is a simplified schematic view of decision tree.

Other than neural networks, another model that may be used for performing machine learning is a decision tree. A decision tree is an example of a supervised machine learning model. Reference is made to FIG. 6, which illustrates an example of a decision tree 200. The decision tree 200 comprises a series of nodes. During the operating phase, input data is provided to the top of the decision tree, and decisions are made on the basis of the data to reach a certain output at the bottom of the tree. The decision tree 200 comprises a root node 205, which represents the start of the decision tree. At the root node 205 a decision is made on the basis of every set of input data fed into the tree, as to which branch of the tree to proceed down for that set of data. The decision made for a first set of data at the root node 205 may cause the decision process to proceed to decision node 210a. On the other hand, a decision made for a second set of data at the root node 205 may cause the decision process to proceed to decision node 210b.

When the process has proceeded to one of the decision nodes 210a, 210b, a decision associated with the particular decision node is then made by applying certain criteria to the set of input data. This decision is then used to determine the next node in the decision tree, to which the process proceeds. This next node may be a further decision node, such as decision node 210c or it may be a terminal node (i.e. a leave), such as terminal nodes 215a, 215b, 215c, 215d, 215e. Each of the terminal nodes represents an output or target value of the decision tree. Hence, by making decisions based on the input values at the root node 205 and each subsequent decision node, the model eventually identifies a terminal node and corresponding output. Hence, decision trees can be used to produce an output from one or more input values.

One type of decision tree is a classification tree, which classifies the one or more input values into a discrete category. Another type of decision tree is a regression tree, where the target variable changes continuously with the input values.

Therefore, as described, a decision tree may be used, during an operating phase, to output a classification and/or a continuous value in dependence upon the input value. During the training phase, the decision tree can be trained by splitting the input data into different subsets based on the values in the input data. The process is repeated on each subset in a recursive manner, until either the data points in a subset at a node in the tree all have the same value for the output or when splitting no longer adds value to the predictions. Once a decision tree is trained, it is then applied to new input data, during an operating phase, to determine previously unknown results.

One limitation present in the use of such decision trees, is their tendency to overfit to the data used to train them. Partitioning the data into subsets until all of the data points correspond to the same output, overfits to the training data, such that poor predictions for future input data sets during the operating phase may result. To overcome this limitation a technique known as a random forest may be applied. A random forest involves, during the training phase, constructing a plurality of decision trees using randomly selected different subsets of the input data. During the operating phase, the same input is provided to each of the decision trees. In the case of classification, the output from the random forest is the mode of the outputs from each of the individual decision trees. On the other hand, in the case of regression analysis, the output from the random forest is the mean of the outputs from each of the individual decision trees. Applying this random forest, where the outputs from a plurality of decision trees are averaged, addresses the problem of overfitting to the data.

Another type of model that may be used for machine learning is a clustering algorithm, such as the k-mean clustering algorithm. This is a type of unsupervised machine learning, which is used to assign different data points into different groups. The algorithm iteratively assigns each data point to one of k groups based on the features that are provided.

Figure 7:
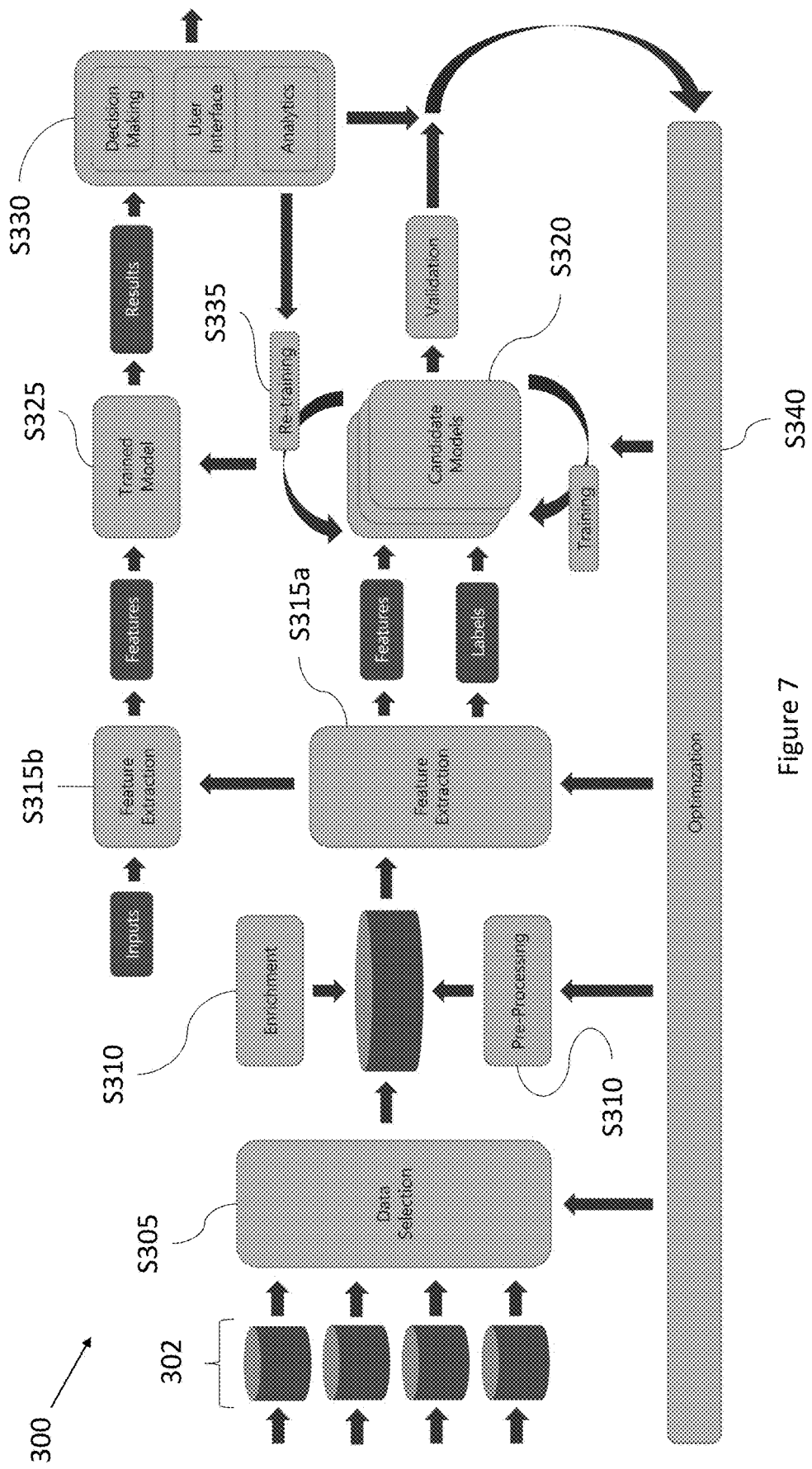
FIG. 7 is a schematic view of the process for training and operating machine learning models.

Reference is made to FIG. 7, which illustrates an overall process 300 by which machine learning can be applied to analyse data. The Figure illustrates one or more data sources 302, which could be, for example, one or more databases storing patient records or a memory storing data input at a terminal. At S305 data is selected from the one or more data sources 302. The data selection is carried out in dependence upon the particular request that is being carried out. For example, a certain set of data may be extracted for estimating a hospital stay time for a patient. A different set of data may be extracted for outputting a possible diagnosis for a patient.

At S310, the selected data is enriched and pre-processed. Enriching the data comprises augmenting the raw data with further information. This information may allow for the data to be interpreted and converted to a standard format. This information may be provided on demand. For example, based on the received raw data, the system determines that further information is required for providing to the machine learning model. This further information can be retrieved and applied to augment the data from the selected raw data.

The pre-processing step involves converting the raw data retrieved at S305 into a standard format that can be analysed. Since the data retrieved at S305 may be retrieved from multiple sources, this retrieved raw data may exist in multiple different formats. By pre-processing the data at S310, the information from the data is converted to a standard format for analysis. The pre-processing carried out at S310 also includes any necessary data cleansing operations. These operations are performed on the raw data to correct or remove any corrupt or inaccurate parts of the data.

At S315*a*, features and labels are extracted from the pre-processed data resulting from S310 to produce a training data set. The feature extraction comprises extracting information that is suitable for providing to a machine learning model from the data to train the model. This stage involves deriving from the data in the standard format, a set of input values (i.e. scores) representing the features for providing to a machine learning model and labels.

These features and labels are used for training one or more models during the training phase. The labels represent expected outputs from a model. Together the feature scores and labels constitute one or more training data sets.

At S320, the features and labels extracted from the data at S315*a* are used to train a model selected from amongst a plurality of candidate models. A candidate model is selected from a set of candidate models that is suitable for performing a particular analysis. For example, a first type of model may be suitable for outputting a possible diagnosis for a patient. Another type of model may be more suitable for estimating the waiting time for a patient. The selected model is trained in a supervised manner using the features and labels extracted at S315*a*. The model selection may be made prior to the feature extraction process, with the features extracted from the data items being dependent upon the selected model.

During training at S320, the parameters (e.g. the weights for a neural network) of the model are tuned so as to reproduce the labels from the features. By doing so, a trained model is produced.

At S315*b*, feature extraction is performed for an operating phase. Input values representing features are determined from a set of data items (as discussed above for steps S305, S310, and S315*a*) and provided to a trained model during an operating phase. The operating data set that is determined at this step does not include the labels present in the training data set. Furthermore, each operating data set is associated with a different event.

At S325, the trained model is applied to the features extracted from a data set provided at S315*b*. The trained model outputs results, which at S330 can be analysed in a number of ways. The results may be displayed to a user on a user interface. The results may be used to inform decision making, e.g. by providing a recommended treatment for a patient. The results may be used to perform further analytics.

At S335, the analysis of the outputs from the models is used to perform re-training of the models. The re-training may be performed in dependence upon data provided at a later date that can be used to optimise the model.

At S340, optimisation of one or more of the stages in the machine learning pipeline is carried out. This optimisation is carried out on the basis of the results and the analysis carried out at S330. For example, indications of the accuracy of the machine learning that are determined by comparing the results of the machine learning to future results ( ) can be used to optimise different stages in the pipeline. The optimisation may involve comparing results from different models and selecting a model from amongst the candidate models in response to determining that this selected model yields superior results to another candidate model.

The optimisation involves optimising any of the other stages in the pipeline, such as modifying the data selection at S305 so as to modify the data selected from the databases 302 for analysis by one or more machine learning models. The optimisation may involve modifying the enrichment stage of the pipeline so that new or different types of data are used for augmenting data sets. The optimisation may involve modifying the format into which raw data is placed during pre-processing. The optimisation may involve modifying the feature extraction performed at S315*a*/S315*b*, so that different features are extracted or that different input values are used to represent the features.

Figure 8:
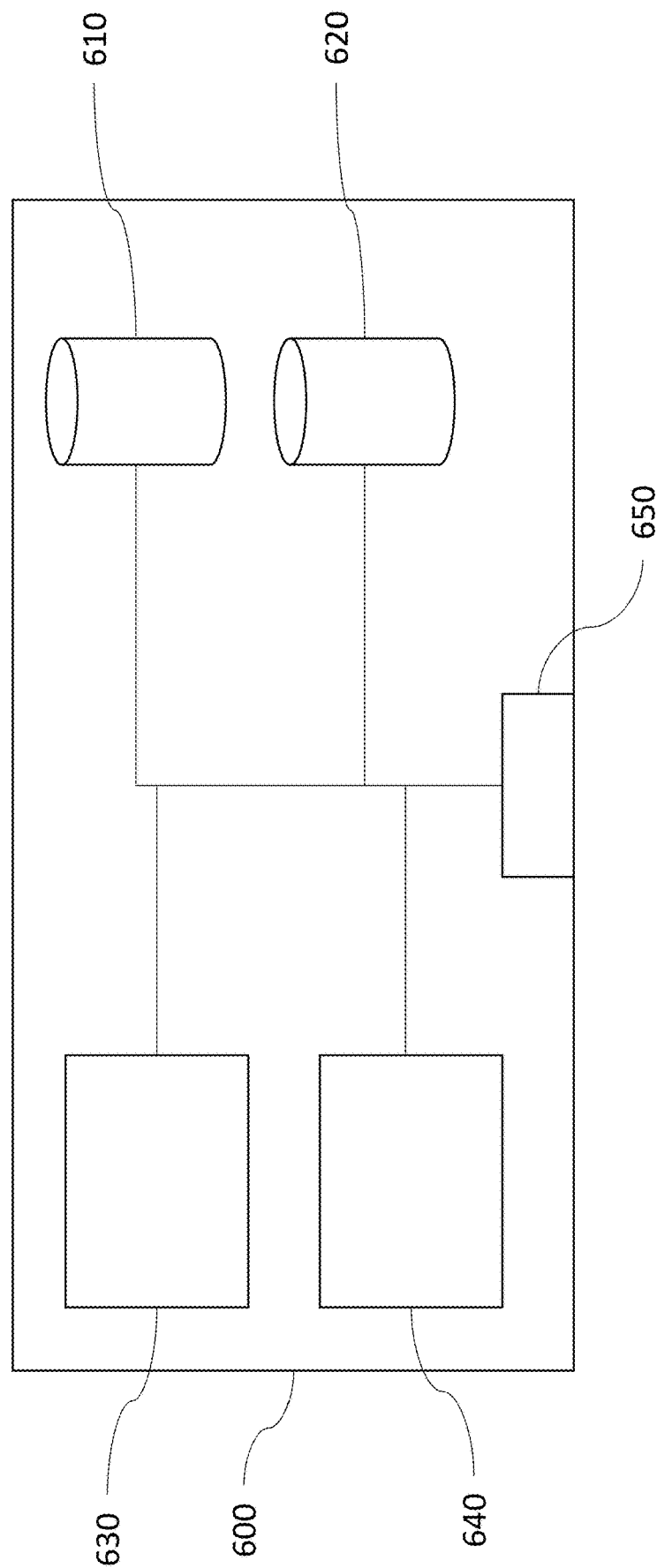
FIG. 8 is a schematic view of a system for implementing a process for training and operating machine learning models.

Reference is made to FIG. 8, which illustrates a data processing system 600, in which embodiments of the application may be implemented. The system 600 provides one or more machine learning models, and may execute these model during an operating phase. The system 600 may train these models. The system 600 may provide the system 800 illustrated in FIG. 1A and/or the system 40 illustrated in FIG. 1.

The system 600 is shown as a single enclosed apparatus. However, in some embodiments, the system 600 is a distributed system, with multiple data processing apparatuses operating in communication with one other. The system 600 may comprise a server, back-end system, or the like for performing processing on behalf of one or more client devices.

The system 600 comprises at least one random access memory 610, at least one read only memory 620, at least one data processing unit 640, 630 and an input/output interface 650.

The memories 610, 620, store data for inputting to the one or more models and for storing results of the processing performed during execution of the one or more models. At least one of the memories 610, 620 store data items associated with the patients and the operating data that is obtained from the data items by the conversion module. At least one of the memories 610, 620 additionally store computer executable code which, when executed by at least one data processing unit 620, 630, provide the one or more machine learning models and the conversion module. At least one of the data processing units 630, 640 performs one or more of: the processing associated with the one or more models, the training of the models, and any necessary pre-processing of data for use by the models. At least one of the data processing units 630, 640 execute the computer executable code to provide the one or more models, the API, conversion module, and model supervisor. Via the interface 650, the system 600 receives the data items for constructing the training data sets and/or the data items for constructing the operating data sets. The system 600 additionally sends via the interface 650, the results produced by running the models on input data.

Therefore the described example embodiments of the application may be implemented by one or more of the data processing units 620, 630 of the system. The data processors may be of any type suitable to the local technical environment, and may include one or more of general purpose computers, special purpose computers, microprocessors, digital signal processors (DSPs), application specific integrated circuits (ASIC), gate level circuits and processors based on multi core processor architecture, as non-limiting examples. An appropriately adapted computer program code product or products may be executed on one or more of the data processing units 620, 630 for implementing the example embodiments. The program code product for providing the operation may be stored on, provided and embodied by means of an appropriate carrier medium.

Figure 9:
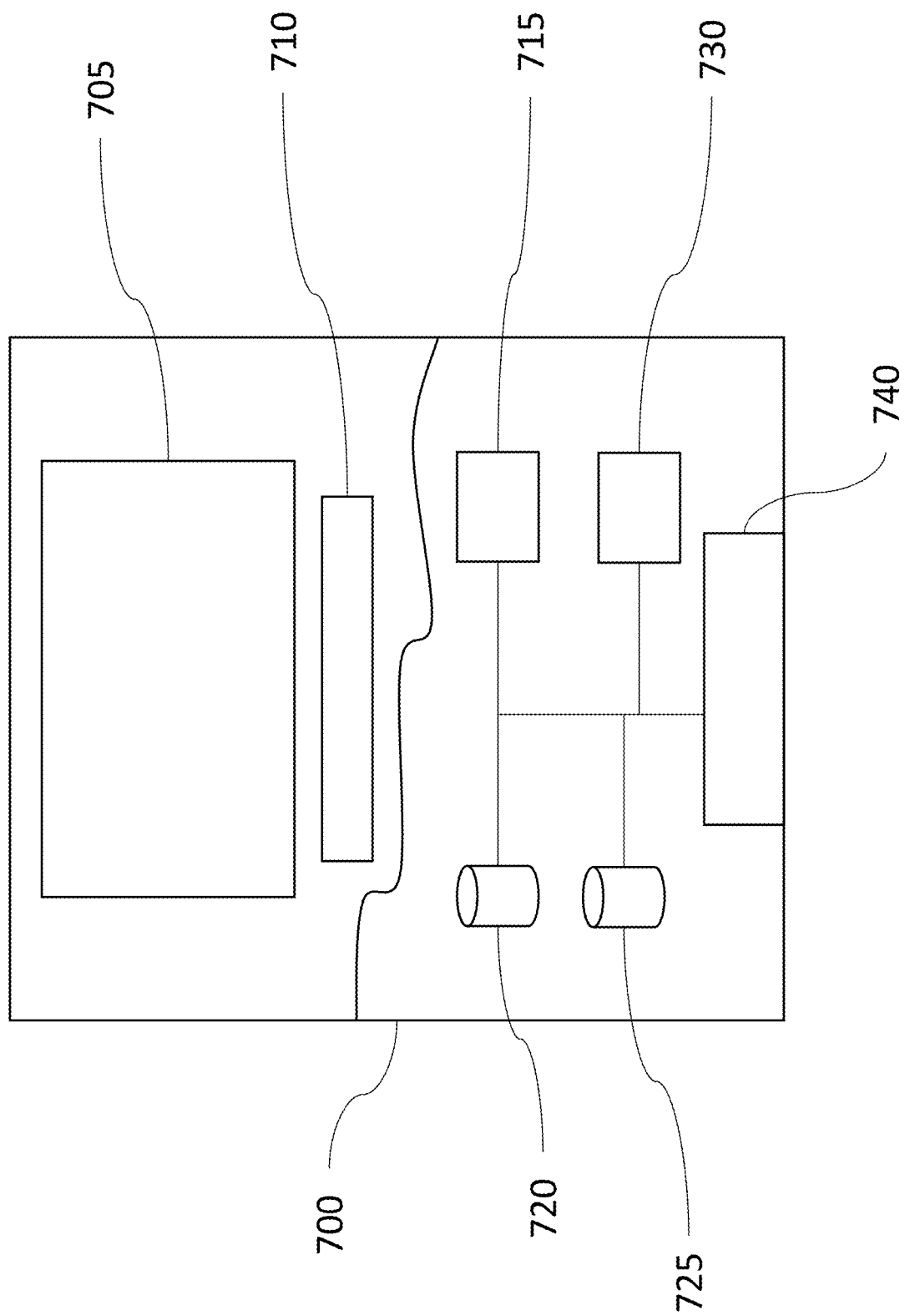
FIG. 9 is a schematic view of a user device for interacting with the system.

As noted, the system 600 on which data is processed using the one or more models may perform the processing on behalf of one or more client devices or terminals (e.g. triaging terminals) that are configured to communicate with the system 600. Reference is made to FIG. 9, which illustrates an example of an electronic device 700, which functions as such a client device 700. The electronic device 700 may be a mobile user equipment (UE), a personal computer (PC), a terminal or workstation or some other form of device. The device 700 may provide any of the triaging terminals 25 illustrated in FIG. 1.

The device 700 comprises an interface 740 over which it sends and receive signals with the system 700. The interface 740 may be a transceiver apparatus configured to send and receive communications over a radio interface. The transceiver apparatus may be provided, for example, by means of a radio part and associated antenna arrangement. The antenna arrangement may be arranged internally or externally to the device 700.

The device 700 is provided with at least one data processing entity 715, at least one random access memory 720, at least one read only memory 725, and other possible components 730 for use in software and hardware aided execution of tasks it is designed to perform, including control of, access to, and communications with access systems and other communication devices. The at least one random access memory 720 and the at least one read only memory 725 may be in communication with the data processing entity 715, which may be a data processor. The data processing, storage and other relevant control apparatus can be provided on an appropriate circuit board and/or in chipsets. A user may control the operation of the device 700 by means of a suitable user interface such as key pad 710, voice commands, touch sensitive screen or pad, combinations thereof or the like. A display 705, a speaker and a microphone can be also provided in the device 700. The display 705 enables a user to select data for processing by the system 600 and/or view results of the processing. Furthermore, the device 700 may comprise appropriate connectors (either wired or wireless) to other devices and/or for connecting external accessories, for example hands-free equipment, thereto.

At least one of the memories 720, 725 may be configured to store at least some of the data items that are used by the system 600 to construct the operating and/or training data sets. The at least one data processing entity 715 is configured to cause these data items to be sent via interface 730 to the system 600 for processing. The at least one data processing entity 715 may additionally or alternatively cause the sending of an instruction via interface 730 to cause data items to be retrieved from a further entity 600 and delivered to the system for constructing operating and/or training data sets.

The device 700 may additionally receive results (e.g. assignment of medical resources to a patient) of processing by one or more machine learning models operating on the system 600. These results are received by the interface 730 and stored in at least one of the memories 720, 725. The results may be displayed to a user of the device 700 on the display 705.

The invention claimed is:

1. A computer system for controlling a patient's access to a medical resource, the system comprising at least one processor configured to:

provide at least one trained machine learning model which has been trained on a first training data set comprising healthcare event associated data, the at least one trained machine learning model having an input for receiving at least one operating data set associated with a particular healthcare event and an output for generating at least one value associated with the particular healthcare event, the at least one operating data set being obtained from a set of data items associated with the particular healthcare event, the set of data items including data items comprising:

patient-level clinical data; and
temporal data containing time-dependent data regarding the particular healthcare event and describing a state of healthcare facilities and/or external systems at a given point in time,
wherein:
the data items include data accessed from a data store; and
the temporal data accessed from the data store comprises a first indication of availability of healthcare resources;
generate the at least one operating data set in dependence upon the data accessed from the data store;
provide the at least one operating data set to the at least one trained model and receive the at least one value, the at least one value comprising:
a second indication of the availability of the healthcare resources;
generate, based on the at least one value, a first treatment recommendation of the medical resource for assignment to the patient;
in dependence upon the first treatment recommendation, generate an initial indication of an assignment of the medical resource for the patient associated with the particular healthcare event;
subsequent to assigning the medical resource for the patient, receive an indication of an outcome of the treatment recommendation for the patient;
generate a further operating data set that comprises the at least one operating data set and the outcome of the treatment recommendation; and
provide the further operating data set to a further trained machine learning model to generate a second indication of an assignment of the medical resource,
wherein the initial indication of the assignment of the medical resource comprises a test to be carried out on the patient and wherein the further operating data set comprises the first operating data set augmented by including a score derived from the results of the test; and
wherein the first training data set comprises an array, the array including:
a plurality of rows; and
a plurality of columns,
wherein each intersection between one row of the plurality of rows and one column of the plurality of columns contains a feature score, the feature score being associated with:
one healthcare event of a plurality of healthcare events; and
one feature of a plurality of features associated with the plurality of healthcare events or one label of a plurality of labels associated with the plurality of healthcare events.

2. A computer system as claimed in claim 1, wherein the at least one processor is configured to:
request the data from the data store in dependence upon data input at a client device.

3. A computer system as claimed in claim 1, wherein the data requested from the data store comprises data retrieved from an electronic health record of the patient.

4. A computer system as claimed in claim 1, wherein the at least one value comprises at least one probability associated with one or more diagnoses for the patient.

5. A computer system as claimed in claim 1, wherein the at least one value comprises a predicted outcome associated with the particular healthcare event.

6. A computer system as claimed in claim 1, wherein the at least one trained machine learning model comprises a plurality of trained machine learning models, each of the plurality of models having an input for receiving an operating data set associated with the particular healthcare event and an output for generating at least one value associated with the particular healthcare event,
wherein the at least one processor is configured to:
provide a first operating data set to a first of the models to generate a first at least one value;
provide a second operating data set to a second of the models to generate a second at least one value; and
in dependence upon both the first at least one value and the second at least one value, generate an indication of an assignment of medical resources for the patient associated with the event.

7. A computer system as claimed in claim 1, wherein the at least one processor is configured to provide one or more further operating data sets to the at least one trained model to obtain one or more further values, wherein each of the one or more further operating data sets is associated with a different patient,
wherein the generation of an indication of an assignment of medical resources for the patient associated with the event is performed in dependence upon the one or more further values.

8. A computer system as claimed in claim 7, wherein the at least one value comprises an indication of a value of assigning a first medical resource to the patient associated with the event, wherein at least one of the one or more further values comprises an indication of a value of assigning the first medical resource to a further patient,
wherein the generation of an indication of an assignment of medical resources for the patient associated with the event comprises comparing the value of assigning the first medical resource to the patient associated with the event with the value of assigning the first medical resource to the further patient so as to prioritise access to the first medical resource.

9. A computer system as claimed in claim 7, wherein the at least one processor is configured to provide a third operating data set to the at least one trained model to obtain an indication of a value of assigning a second medical resource to the patient associated with the event,
wherein the generation of the indication of the assignment of medical resources for the patient associated with the event is performed in dependence upon the value of assigning the second medical resource to the patient associated with the event.

10. The computer system of claim 6, wherein:
the at least one trained machine learning model comprises:
a first trained machine learning model; and
a second trained machine learning model;
the array is a first array to facilitate training of the first trained machine learning model, the plurality of rows is a first plurality of rows, the plurality of columns is a first plurality of columns, the plurality of features is a first plurality of features, the plurality of labels is a first plurality of labels, and respective feature scores of the first array are first feature scores; and
a second training data set comprises a second array to facilitate training of the second trained machine learning model, the second array including:
a second plurality of rows; and
a second plurality of columns, wherein:
each intersection between one row of the second plurality of rows and one column of the second plurality of columns contains a second feature score, the second feature score being associated with:
one healthcare event of the plurality of healthcare events; and
one feature of a second plurality of features associated with the plurality of healthcare events or one label of a second plurality of labels associated with the plurality of healthcare events; and
the first and second plurality of features are different and/or the first and second plurality of labels are different.

11. The computer system of claim 10, wherein:
the set of data items is a first set of data items;
the at least one operating data set includes at least one feature;
the outcome of the treatment recommendation includes at least one label; and
the at least one processor is configured to, when generating the second training data set:
retrieve additional data from the data store;
generate, using the additional data, a second set of data items in a standard format;
generate at least one feature score for each of the at least one feature and the at least one label by applying a transformation to the second set of data items.

12. The computer system of claim 11, wherein the at least one processor is configured to, when generating the at least one feature score by applying the transformation to the second set of data items:
count a number of times a first data item of the second set of data items appears within the second set of data items; and generate the at least one feature score in proportion to the count.

13. The computer system of claim 11, wherein the at least one processor is configured to, when retrieving the additional data:
retrieve first additional data from the data store;
generate, using the first additional data, a request for second additional data;
transmit the request to an additional data source; and
retrieve, from the additional data source in response to the request, the second additional data,
wherein the additional data includes the first and second additional data.

* * * * *